US012718929B2

(12) United States Patent
Scherrer et al.

(10) Patent No.: US 12,718,929 B2
(45) Date of Patent: Aug. 25, 2026

(54) IDENTIFYING MEDICAL IMAGING PROTOCOLS BASED ON RADIOLOGY DATA AND METADATA

(71) Applicant: Quantivly Inc., Somerville, MA (US)

(72) Inventors: Benoit Scherrer, Somerville, MA (US); Robert D. MacDougall, La Mesa, CA (US); Dimitri Falco, Dexter, MI (US)

(73) Assignee: Quantivly Inc., Somerville, MA (US)

( * ) Notice: Subject to any disclaimer, the term of this patent is extended or adjusted under 35 U.S.C. 154(b) by 547 days.

(21) Appl. No.: 18/142,820

(22) Filed: May 3, 2023

(65) Prior Publication Data

US 2023/0360777 A1 Nov. 9, 2023

Related U.S. Application Data

(60) Provisional application No. 63/442,576, filed on Feb. 1, 2023, provisional application No. 63/337,827, filed on May 3, 2022.

(30) Foreign Application Priority Data

Feb. 1, 2023 (FR) .................................. FR2300941

(51) Int. Cl.
*G16H 30/40* (2018.01)
*G16H 30/20* (2018.01)

(52) U.S. Cl.
CPC ............. *G16H 30/40* (2018.01); *G16H 30/20* (2018.01)

(58) Field of Classification Search
CPC ............................... G16H 30/40; G16H 30/20
(Continued)

(56) References Cited

U.S. PATENT DOCUMENTS 6,603,494 B1 8/2003 Banks
6,988,074 B2 1/2006 Koritzinsky
(Continued)

FOREIGN PATENT DOCUMENTS

DE 10126571 1/2002
DE 102017203315 A1 * 9/2018 ............. G16H 30/20
(Continued)

OTHER PUBLICATIONS

Manojlovi'c, T.; Štajduhar, I. Deep Semi-Supervised Algorithm for Learning Cluster-Oriented Representations of Medical Images Using Partially Observable DICOM Tags and Images. Diagnostics 2021, 11, 1920. https://doi.org/10.3390/diagnostics 11101920 (Year: 2021).*
(Continued)

*Primary Examiner* — Xiao Liu
*Assistant Examiner* — Eric James Shoemaker
(74) *Attorney, Agent, or Firm* — Blueshift IP; Robert Plotkin

(57) ABSTRACT

A computer-implemented method uses a plurality of input examination data sets, created by performing a plurality of imaging examinations of at least one patient on at least one scanner, to learn a model of imaging protocols. The model may learn imaging protocols by capturing common features across the plurality of input examination data sets. The method may regroup examination data sets, within the plurality of input examination data sets, with common features under a common protocol tag, and learning the model may include generating a plurality of protocol tags. The model may be updated over time based on new input examination data sets.

22 Claims, 9 Drawing Sheets

(58) Field of Classification Search
USPC .......................................................... 382/128
See application file for complete search history.

(56) References Cited

U.S. PATENT DOCUMENTS

| | | | | |
|---|---|---|---|---|
| 7,542,792 | B2 | 6/2009 | Wollenweber | |
| 7,676,463 | B2 * | 3/2010 | Thompson | G06F 16/355 707/999.005 |
| 7,685,262 | B2 | 3/2010 | Choubey | |
| 7,885,828 | B2 | 2/2011 | Glaser-Seidnitzer | |
| 8,705,819 | B2 | 4/2014 | Carlsen | |
| 9,262,514 | B2 * | 2/2016 | Eckardt, III | G06F 16/338 |
| 9,317,580 | B2 | 4/2016 | Cohen-Solal | |
| 10,049,301 | B2 | 8/2018 | Kluckner | |
| 10,324,594 | B2 | 6/2019 | Meyer | |
| 10,346,586 | B2 | 7/2019 | Seethamraju | |
| 10,470,739 | B2 | 11/2019 | Raman | |
| 10,600,136 | B2 | 3/2020 | Cohen-Solal | |
| 10,709,407 | B2 | 7/2020 | Stevens | |
| 2006/0269167 | A1 * | 11/2006 | Venkatesan | G06V 30/1988 382/218 |
| 2008/0119717 | A1 | 5/2008 | Profio | |
| 2014/0221832 | A1 | 8/2014 | El-Zehiry | |
| 2014/0379410 | A1 | 12/2014 | Lee | |
| 2015/0081315 | A1 | 3/2015 | Baker | |
| 2017/0185713 | A1 * | 6/2017 | Bhatia | G16H 30/20 |
| 2018/0254098 | A1 * | 9/2018 | Allmendinger | G16H 50/50 |
| 2019/0074083 | A1 | 3/2019 | Jung | |
| 2020/0020098 | A1 | 1/2020 | Odry | |
| 2020/0043616 | A1 | 2/2020 | Saalbach | |
| 2020/0097767 | A1 | 3/2020 | Perry | |
| 2021/0035296 | A1 | 2/2021 | Mahrooghy | |
| 2021/0059631 | A1 | 3/2021 | Lewis | |
| 2021/0118554 | A1 | 4/2021 | Amthor | |
| 2021/0193331 | A1 * | 6/2021 | Raman | G16H 30/20 |
| 2023/0222771 | A1 * | 7/2023 | Beaumont | G06V 10/26 382/128 |

FOREIGN PATENT DOCUMENTS

| | | | | |
|---|---|---|---|---|
| EP | 3696819 | A1 * | 8/2020 | G16H 50/70 |
| JP | 6747804 | | 8/2020 | |
| KR | 20150002284 | | 1/2015 | |
| KR | 20190109141 | | 9/2019 | |
| KR | 20200041813 | | 4/2020 | |
| WO | WO-2017151759 | A1 * | 9/2017 | G06N 3/045 |
| WO | WO-2019040534 | A1 * | 2/2019 | G06V 20/698 |
| WO | 2021108398 | | 6/2021 | |

OTHER PUBLICATIONS

Gauriau R, Bridge C, Chen L, Kitamura F, Tenenholtz NA, Kirsch JE, Andriole KP, Michalski MH, Bizzo BC. Using DICOM Metadata for Radiological Image Series Categorization: a Feasibility Study on Large Clinical Brain MRI Datasets. J Digit Imaging. Jun. 2020;33(3):747-762. (Year: 2020).*

2018D Edition of DICOM. PS3.3. https://dicom.nema.org/medical/dicom/2018d/output/chtml/part03/chapter_A.html (Year: 2018).*

Safaei. Text-based multi-dimensional medical images retrieval according to the features-usage correlation. Med Biol Eng Comput 59, 1993-2017 (2021). https://doi.org/10.1007/s11517-021-02392-0 (Year: 2021).*

International Search Report and Written Opinion issued in App. No. PCT/US2023/020807, mailing date Aug. 28, 2023, 10 pages.

Extended European Search Report issued in App. No. EP23799972 dated Mar. 23, 2026 (pp. 1-13).

* cited by examiner

IDENTIFYING MEDICAL IMAGING PROTOCOLS BASED ON RADIOLOGY DATA AND METADATA

STATEMENT AS TO FEDERALLY SPONSORED RESEARCH

This invention was made with Government support under National Science Foundation (NSF) Grant No. 2036377, awarded to Quantivly, Inc., entitled, "Unified data description layer for magnetic resonance imaging scanners." The Government has certain rights in the invention.

BACKGROUND

Medical imaging scanners (such as Magnetic Resonance Imaging (MRI) scanners, Computerized Tomography (CT) scanners, Positron Emission Tomography (PET) scanners, ultrasound scanners, and X-ray scanners) acquire two- or three-dimensional images of the body. Such images are often used for disease detection, diagnosis, and treatment monitoring.

Such a scanner images the patient in what is referred to as an "imaging acquisition" or simply an "acquisition," which results in one or multiple images (also referred to herein as "acquisition data"). Associated with each such acquisition is a set of corresponding technical parameters, which are specific to the imaging modality (e.g., MRI or CT) that is employed during the acquisition. The values of those technical parameters (e.g., in MRI: echo time and repetition time, among others; in CT: kVp and mAs, among others) define a variety of settings and factors that affect the quality and characteristics of the final images, including which specific tissue properties are being assessed during the acquisition, ultimately leading to different views of the tissues imaged (e.g., T1-weighted, T2-weighted). During an "examination" (also referred to herein as an "imaging examination") the patient may undergo one or multiple acquisitions so that different, typically complementary, views of the tissues are assessed. The term "imaged protocol" refers herein to a plurality of acquisition data sets that were acquired in a particular examination. The term "examination data set" refers herein to the following, which are associated with a particular examination: (1) a plurality of acquisition data sets that represent the acquisitions performed in a particular examination (i.e., the imaged protocol) corresponding to the examination data set; and (2) (optionally) one or more non-technical parameters, and their associated values, associated with the examination.

Radiologists typically build ideal protocols based on radiologist diagnostic requirements, within certain constraints, such as time, patient safety (e.g., SAR or radiation dose), and patient tolerance/satisfaction. Such ideal protocols are designed to study each clinical indication (e.g., diagnostic question, such as brain tumor, brain multiple sclerosis, brain presurgical planning). Such ideal protocols may differ for different patient demographics (e.g., age, BMI). We refer to each such ideal protocol as a "parent protocol."

Unfortunately, some scanners may have technical limitations which impair their ability to perform some acquisitions specified in a parent protocol. For example, a particular parent protocol may include an acquisition with parameter and value which a particular scanner cannot implement. As a result, to perform the acquisition on that scanner requires modifying the protocol for use with that scanner, such as by changing the parameter value or applying a different parameter on that scanner. The result is a modified version of the parent protocol, which is referred to herein as a "child protocol." Child protocols may, for example, be created on the fly by modifying the parameters in a scanner, or pre-stored in a scanner in order to reduce preparation time and to increase reproducibility and uniformity of the images produced by the scanners when performing scans using those child protocols. The resulting child protocol may or may not be stored in the scanner for future use.

When the scanner operator images a patient, the operator selects a child protocol from the template list on the scanner. If no custom child protocols have been stored on the scanner, then the child protocol selected by the scanner operator may merely be the default set of parameters and corresponding values of the acquisition as provided by the scanner manufacturer, from which the scanner operator then changes parameters on the fly to match the expected child protocol.

It may be necessary or desirable for the scanner operator to make changes to the child protocol. Examples of changes that the scanner operator may make to the child protocol to produce the imaged protocol include changing values of one or more parameters in the child protocol, and replacing a parameter in the child protocol with a different parameter in the imaged protocol. The child protocol may be changed to produce an imaged protocol for any of a variety of reasons, such as one or more of the following:

- It may be necessary or desirable to change the value of one or more parameters in the child protocol in order to accommodate anatomical features of the patient (e.g., by increasing the number of slices if the patient is larger than was contemplated by the child protocol).
- It may be necessary or desirable for one or more acquisitions to be repeated, such as in the case of patient motion that results in an image being non-diagnostic, thereby resulting in an imaged protocol which contains more acquisitions than the child protocol.
- It may be necessary or desirable to change the order of the acquisitions in the child protocol in order to prioritize some images over others, thereby resulting in an imaged protocol in which the acquisitions are in a different order than in the child protocol.
- It may be necessary or desirable to add a new acquisition, e.g., if there is some suspicion of abnormal tissue and that a new acquisition can help confirm or disconfirm that.

The scanner operator images the patient, thereby resulting in the imaged protocol, which may differ from the child protocol (and the parent protocol). As the description above implies, each imaged protocol is based upon a corresponding child protocol, and may be the same as or differ from that corresponding child protocol. Similarly, each child protocol is based upon a corresponding parent protocol, and may be the same as or differ from that corresponding parent protocol. As this implies, each imaged protocol may be the same as or differ from the parent protocol of its child protocol (i.e., the imaged protocol's "grandparent protocol").

Such a plethora of protocols and their relationships with each other can grow complicated to manage, thereby resulting in a variety of problems. What is needed, therefore, are improved techniques for managing medical scanner protocols.

SUMMARY

A computer-implemented method uses a plurality of input examination data sets, created by performing a plurality of imaging examinations of at least one patient on at least one scanner, to learn a model of imaging protocols. The model may learn imaging protocols by capturing common features across the plurality of input examination data sets. The method may regroup examination data sets, within the plurality of input examination data sets, with common features under a common protocol tag, and learning the model may include generating a plurality of protocol tags. The model may be updated over time based on new input examination data sets.

Other features and advantages of various aspects and embodiments of the present invention will become apparent from the following description and from the claims.

DETAILED DESCRIPTION

A computer-implemented method uses a plurality of input examination data sets, created by performing a plurality of imaging examinations of at least one patient on at least one scanner, to learn a model of imaging protocols. The model may learn imaging protocols by capturing common features across the plurality of input examination data sets. The method may regroup examination data sets, within the plurality of input examination data sets, with common features under a common protocol tag, and learning the model may include generating a plurality of protocol tags. The model may be updated over time based on new input examination data sets.

Figure 10:
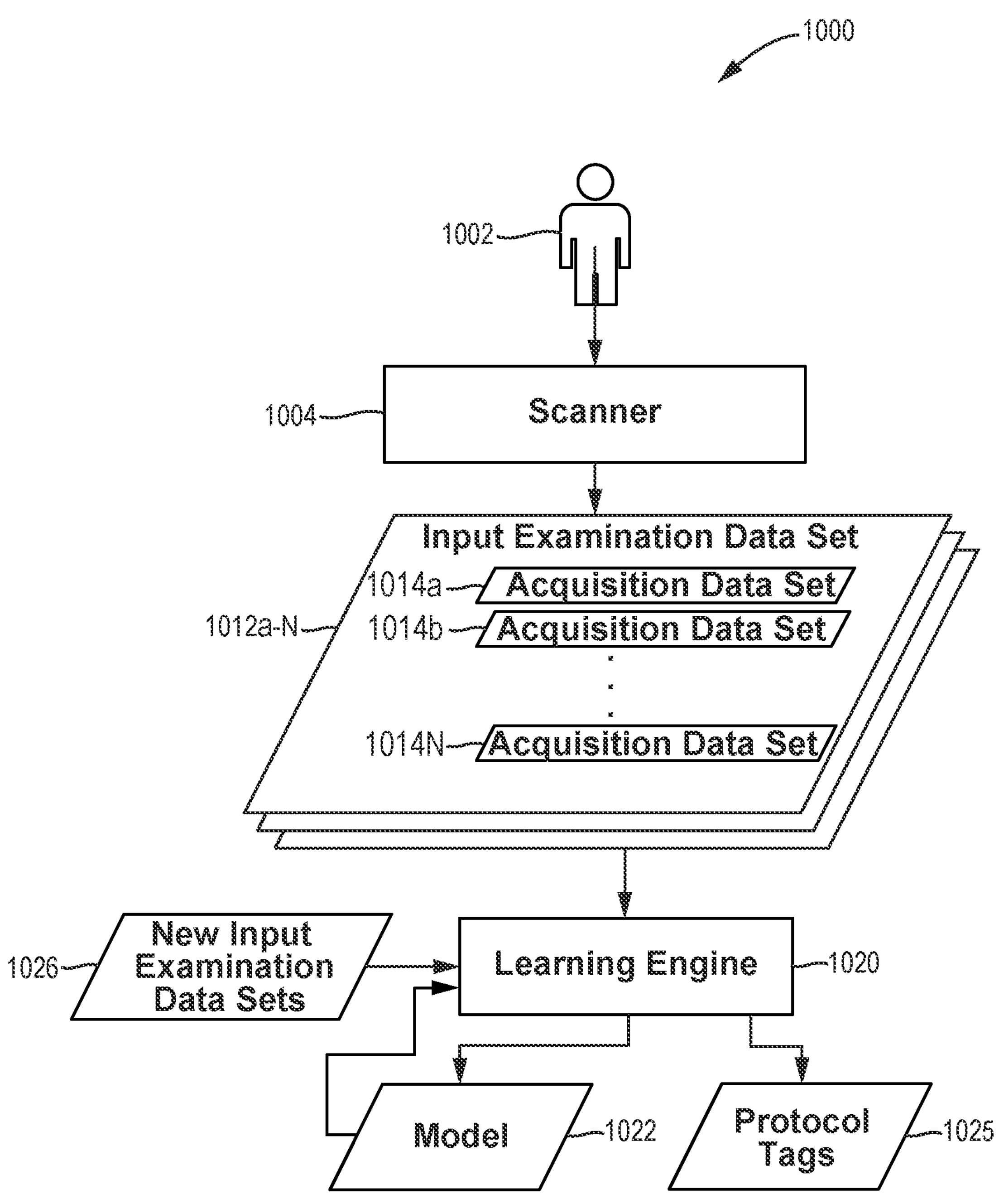
FIG. 10 is a diagram of a system for learning a plurality of protocol tags based on a plurality of examination data sets according to one embodiment of the present invention.
Figure 11:
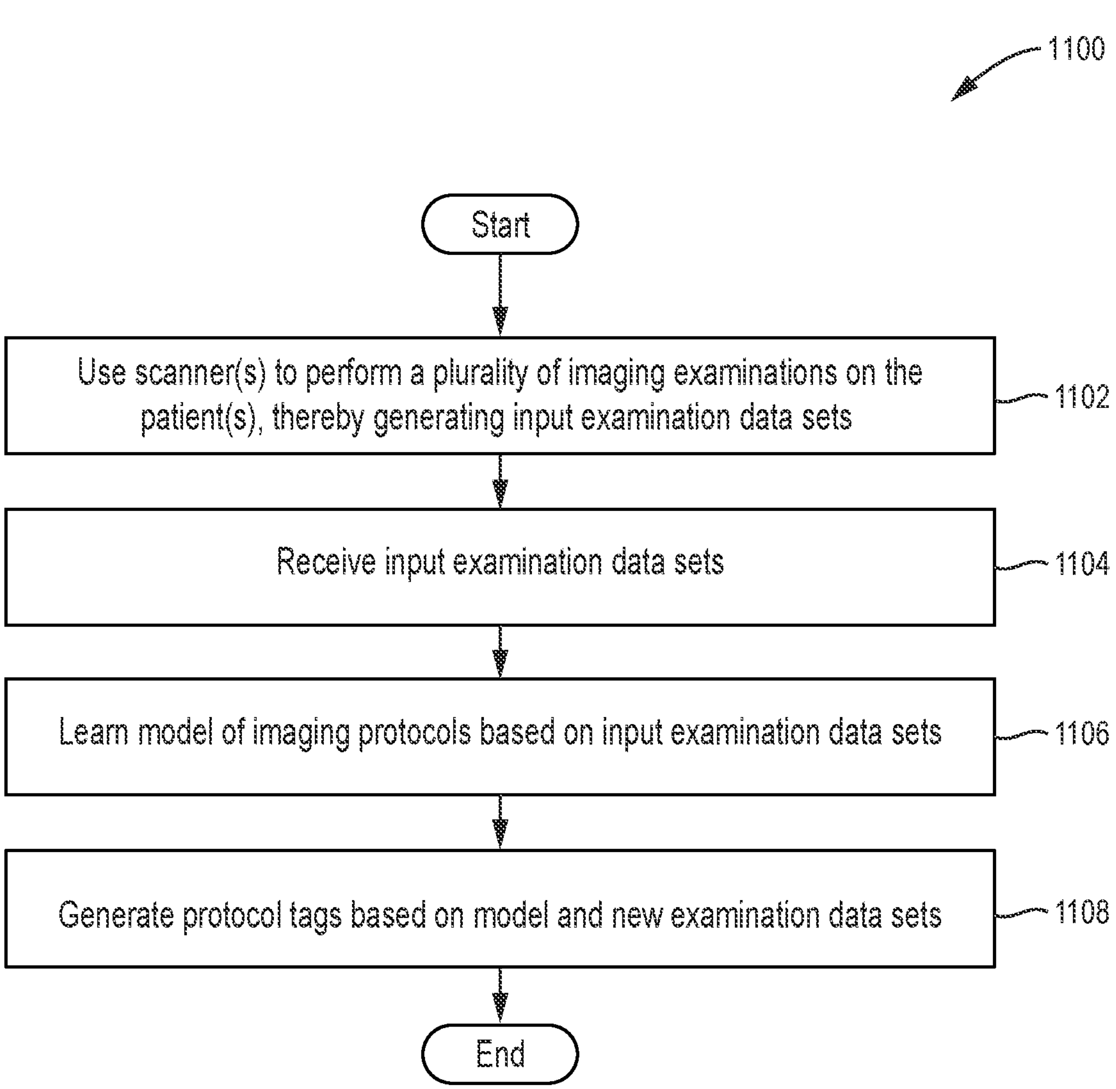
FIG. 11 is a flowchart of a method performed by the system of FIG. 10 according to one embodiment of the present invention.

FIG. 10 is a diagram of a system 1000 for learning a model of imaging protocols based on a plurality of input examination data sets according to one embodiment of the present invention. FIG. 11 is a flowchart of a method 1100 performed by the system 1000 of FIG. 10 according to one embodiment of the present invention.

The system 1000 includes a patient 1002 and a scanner 1004. The system 1000 uses the scanner 1004 to perform a plurality of imaging examinations on the patient 1002, thereby producing a plurality of input examination data sets 1012*a*-N (FIG. 11, operation 1102). As mentioned elsewhere herein, the terms "imaging examination" and "examination" are used interchangeably herein, which implies that the term "examination" refers to an imaging examination. Although only the single patient 1002 is shown in FIG. 10 for ease of illustration, the plurality of examinations may be performed on one or more patients. For example, some of the examinations may be performed on a first patient, and other examinations may be performed on a second patient. Similarly, although only the single scanner 1004 is shown in FIG. 10 for ease of illustration, the plurality of examinations may be performed using one or more scanners. For example, some of the examinations may be performed using a first scanner, and other examinations may be performed using a second scanner.

Each of the plurality of input examination data sets 1012*a*-N includes a plurality of corresponding acquisition data sets. For illustrative purposes only the acquisition data sets 1014*a*-N within examination data set 1012*a* are shown in FIG. 10. However, it should be understood that the other examination data sets 1012*b*-N include their own corresponding pluralities of acquisition data sets. Each acquisition data set A in any of the pluralities of acquisition data sets includes a corresponding plurality of values of a plurality of technical parameters that were used to perform the acquisition that generated the acquisition data set A.

The plurality of input examination data sets 1012*a*-N may include, for example, not only image data and their technical parameters, but also various additional data. Examples of such additional data include any one or more of the following, in any combination:

- Any DICOM (Digital Imaging and Communications in Medicine) data associated with any of the data in the plurality of input examination data sets 1012*a*-N that is not already contained within the image data and their technical parameters, such as DICOM data.
- Any one or more of the M non-technical parameters disclosed herein, such as information obtained from a scheduling system (not shown) that is used to generate and/or store one or more schedules associated with the examinations that are used to generate the examination data sets 1012*a*-N, such as demographic information, whether the patient 1002 is sedated during an acquisition, disease status of the patient 1002, whether the patient 1002 is an in-patient or an out-patient, the patient 1002's body-mass index, the emergency level of an examination, and whether an acquisition is performed with contrast.

The system 1000 also includes a learning engine 1020, which receives the plurality of input examination data sets 1012*a*-N as input (FIG. 11, operation 1104). The learning engine 1020 learns, based on the plurality of input examination data sets 1012*a*-N, a model 1022 of imaging protocols (FIG. 11, operation 1106). The learning engine 1020 may, for example, use supervised learning and/or unsupervised learning to perform the learning in operation 1106.

The model 1022 may, for example, capture common features across at least some of the plurality of input examination data sets 1012*a*-N. The model 1022 may, for example, regroup examination data sets, within the plurality of input examination data sets 1012*a*-N, with common features under a common protocol tag, and learning the model 1022 in operation 1106 may include generating a plurality of protocol tags 1028.

Each of the plurality of protocol tags 1028 may, for example, describe a corresponding set of common features within the plurality of input examination data sets 1012*a*-N, where each of the examination data sets in the set of examination data sets that are regrouped under the protocol tag have a corresponding set of common features that are described by the protocol tag. The plurality of protocol tags 1028 may, for example, include a plurality of embeddings (e.g., a plurality of embeddings of fixed size). In this case, the corresponding set of common features is determined by a clustering algorithm grouping embeddings within a pre-defined proximity. A protocol tag may also be considered a "label," as that term is used elsewhere herein.

Although generating the protocol tags 1028 is shown as part of the method 1100 in FIG. 11, which also includes learning the model 1022, in practice the protocol tags 1028 need not be generated as part of the same process (or by the same entity) that learns the model 1022. For example, one process may learn the model 1022, and another process may use the model to generate the protocol tags 1028. As a particular example, one entity may learn the model 1022, and another entity (which did not learn the model 1022) may use the model 1022 to generate the protocol tags 1028.

Furthermore, although FIGS. 10 and 11 show the protocol tags 1028 being generated based on the model 1022, more generally the protocol tags 1028 may be generated in any of a variety of ways based on the input examination data sets 1012*a*-N and/or the new input examination data sets 1026. For example, even if the protocol tags 1028 are generated based on the model 1022 as described above, in such a case the protocol tags 1028 are generated indirectly based on the input examination data sets 1012*a*-N and/or the new input examination data sets 1026.

The system 1000 may also include a plurality of new input examination data sets 1026. Although the plurality of new input examination data sets 1026 are not shown in detail in FIG. 10, the plurality of new input examination data sets 1026 may have any of the features disclosed herein in connection with the plurality of input examination data sets 1012*a*-N. For example, each examination data set in the plurality of new input examination data sets 1026 may include a plurality of acquisition data sets of the kind disclosed herein. The content of the plurality of new input examination data sets 1026 (e.g., images, technical parameters and parameter values, and non-technical parameters and parameter values) may be the same as or differ from the content of the plurality of input examination data sets 1012*a*-N in any way. The plurality of new input examination data sets 1026 may, for example, be generated after operation 1106 has been performed to generate at least an initial version of the model 1022.

The learning engine 1020 may generate, using the model 1022 and the plurality of new input examination data sets 1026, the plurality of protocol tags 1028 (FIG. 11, operation 1108). Each of the plurality of protocol tags 1028 may describe a corresponding set of common features within the plurality of new input examination data sets 1026.

Each tag T in the plurality of protocol tags 1028 describes a corresponding set of examination data sets in the plurality of input examination data sets 1012*a*-N, where that corresponding set of examination data sets includes a plurality of acquisition data sets that share a corresponding set of common features within the plurality of input examination data sets 1012*a*-N.

Although the plurality of new input examination data sets 1026 is shown in FIG. 10 as a single plurality of new input examination data sets 1026 for ease of illustration, in practice the plurality of new examination data sets 1026 may include multiple pluralities of new input examination data sets, and any of the functions that are disclosed herein as being performed on the plurality of new input examination data sets 1026 (e.g., generating the protocol tags 1028 based on the plurality of new input examination data sets 1026) may be performed on any subset of the plurality of new input examination data sets 1026. As an example, the plurality of new input examination data sets 1026 may include a first plurality of new input examination data sets at a first time (e.g., as a result of performing a first set of imaging examinations using the scanner 1004), and the system 1000 may process the first plurality of new input examination data sets to perform a particular function, such as generating a first set of protocol tags within the protocol tags 1028. At a later, second, time, the plurality of new input examination data sets 1026 may include a second plurality of new input examination data sets (e.g., as the result of performing additional imaging examinations using the scanner 1004), and the system 100 may process the second plurality of new input examination data sets to perform a particular function, such as: (1) generating the corresponding set of protocol tags within the protocol tags 1028 or (2) updating the model 1022 (using any of the techniques disclosed herein the learn the model 1022) to generate an updated version of the model 1022 (and, optionally, as a byproduct of updating the model 1022, generating the corresponding set of protocol tags within the protocol tags 1028). As these examples illustrate, the plurality of new input examination data sets 1026 may change over time, and various functions disclosed herein may process some or all of the plurality of new input examination data sets in the state at which it exists at any particular time.

The learning performed by the learning engine 1020 in operation 1106 to learn the model 1022 may include: (1) learning a first set of protocol tags from the plurality of input examination data sets 1012*a*-N; and (2) learning a second set of protocol tags from the plurality of input examination data sets 1012*a*-N and the first set of protocol tags, where the second set of protocol tags describes a corresponding set of common features of a corresponding plurality of protocol tags within the first set of protocol tags. The plurality of protocol tags 1028 may include the first set of protocol tags and the second set of protocol tags. Step (2) may include learning what is described herein as a "child protocol" from a "parent protocol" or vice versa. Step (2) may be repeated any number of times in connection with any first and second sets of protocol tags, such as protocol tags that were learned in previous instances of step (2) and which may, for example, present new information suggesting new insight on the previously-learned set of protocol tags. The learning process may as such occur repeatedly, at any depth, until, for example, all possible unique common sets are isolated.

The learning performed by the learning engine 1020 in operation 1106 to learn the model 1022 may include, starting with N=1:(1) learning an Nth set of protocol tags from the plurality of examination data sets and from any previously-learned set(s) of protocol tags for N≥1, wherein the Nth set of protocol tags describes a corresponding set of common features of a corresponding plurality of (N−1)-level protocol tags; (2) determining whether a termination criterion has been satisfied; (3) if the termination criterion has been satisfied, then terminating the learning; (4) if the termination criterion has not been satisfied, then: (4) (a) incrementing N; and (4) (b) returning to (1).

The learning performed by the learning engine 1020 in operation 1106 to learn the plurality of protocol tags 1028 may include learning, based on the plurality of input examination data sets 1012*a*-N, a classifier or a clustering algorithm for identifying characteristics of the plurality of input examination datasets 1012*a*-N; and learning the plurality of protocol tags 1028 may include using the classifier or the clustering algorithm to learn the plurality of protocol tags 1028.

The method 1100 may also identify, for each of the plurality of protocol tags 1028, a corresponding organ of interest, thereby identifying a plurality of organs of interest corresponding to the plurality of protocol tags 1028. The method 1100 may identify, for each of the plurality of protocol tags 1028, a label. Some or all of the input examination data sets 1012*a*-N may be labelled, and identifying the label associated with each of the plurality of protocol tags 1028 may include identifying that label based on labeled examination data sets within the plurality of input examination data sets 1012*a*-N. The plurality of organs of interest corresponding to the plurality of protocol tags may, for example, be identified by applying learning to a plurality of images, such as some or all of the images in the plurality of input examination data sets 1012*a*-N.

The method 1100 (e.g., the learning engine 1020) may also (e.g., before generating the model 1022 in operation 1106) generate, for each input examination data set in the plurality of input examination data sets 1012*a*-N, a corresponding graph. Generating such graphs may include, for example, for each input examination data set in the plurality of input examination data sets 1012*a*-N:

- for each of a plurality of a plurality of nodes in the graph corresponding to a plurality of acquisition data sets in the input examination data set, storing information about the acquisition corresponding to the node; and
- for each pair of nodes in the corresponding graph, generating and storing an edge in the graph representing information about a relationship between the pair of nodes.

The result of such a process may generate a plurality of graphs corresponding to the plurality of input examination data sets 1012*a*-N.

Any of a variety of information may be stored in each node corresponding to an acquisition, such as information about some or all of the acquisition's technical parameters and/or information about some or all of the acquisition's non-technical parameters. Information about a parameter may include, for example, an identifier of the parameter and/or a value of the parameter.

Any of a variety of information may be stored in each edge, such as a distance between the pair of nodes connected by the edge and/or a distance or similarity between the pair of nodes connected by the edge.

Any of a variety of information may be stored in a graph as one or more global graph features. For example, in a graph representing an examination, information representing the examination's non-technical parameters may be stored in the graph's global graph features.

If such a plurality of graphs is generated, learning the model 1022 in operation 1106 may include performing learning based on the corresponding plurality of graphs to generate a corresponding plurality of embeddings representing the plurality of protocol tags 1028.

Whether or not the method 1100 generates the plurality of graphs, after the method 1100 learns the model in operation 1106, the method 1100 (e.g., the learning engine 1020) may learn, based on some or all of the plurality of new input examination data sets 1026, an updated version of the model 1022 (not shown in FIG. 10). For example, the system 1000 may generate the plurality of new input examination data sets 1026 by performing a new plurality of imaging examinations of at least one patient (e.g., the patient 1002) on at least one scanner (e.g., the scanner 1004), and the learning engine 1020 may learn the updated version of the model 1022 based on the plurality of new input examination data sets 1026 generated as a result of performing such a new plurality of imaging examinations. As described earlier, this is merely one example of a way in which the plurality of new input examination data sets 1026 may be generated/updated over time, and in which the plurality of new input examination data sets 1026 may be processed. Examination data sets within the plurality of new input examination data sets 1026 may be used both to generate the protocol tags 1028 and to learn the updated version of the model 1022.

In embodiments in which the system 1000 and method 1100 generate the corresponding plurality of embeddings, the system 1000 and method 1100 may generate, for the corresponding plurality of embeddings, a graph corresponding to the corresponding plurality of embeddings. Generating such a graph may include, for example:

- for each node in a plurality of nodes in the graph corresponding to the plurality of embeddings, storing information about an embedding corresponding to the node; and
- for each pair of nodes in the corresponding graph, generating and storing an edge in the corresponding graph representing information about a relationship between the pair of embeddings.

As described in more detail elsewhere herein, embodiments of the present invention may generate and store graphs at increasingly high levels, such as by generating first-level graphs representing examination data sets (in which the nodes in each graph contain information about the acquisition data sets in the examination data set that corresponds to the graph) and by generating second-level graphs representing collections of examination data sets (in which the nodes in each graph contain information about (e.g., an embedding) the examination data sets in the collection of examination data sets that corresponds to the graph). This process may continue to generate even high-level graphs, in which individual graphs at a lower level correspond to nodes at a higher level.

Learning the model 1022 in operation 1106 may further include performing learning on the corresponding graph generated to generate a plurality of high level embeddings.

In embodiments which include a plurality of embeddings, the method 1100 may further include generating, based on the plurality of embeddings, at least one synthetic examination data set, wherein the plurality of input examination data sets does not include the synthetic examination data set. This may be used, for example, to generate a version of an imaging protocol for a different scanner or patient demographic; to average a plurality of imaging protocols; to suggest an imaging protocol less prone to patient motion; or to generate an equivalent protocol that is faster to acquire.

The model 1022 has many applications. For example, the model 1022 may be used to:

- detect deviations in imaging protocols on a scanner and, in response to such detection, to alert the user early in order to prevent "protocol creep" (e.g., imaged protocols which deviate too far from their corresponding parent/child protocols);

provide an overview of child and parent imaging protocols in order to help harmonize protocols across scanner models and scanner vendors; and assess statistics for each imaging protocol (e.g., average protocol duration and variability) and slice the data in order to gain detailed insight about each imaging protocol (e.g., average duration per scanner, per patient demographics, per operator demographics).

More generally, by generating the model 1022, which may relate parent, child, and imaged protocol within an examination data set, embodiments of the present invention provide a key building block that is needed for many applications that can be built on top of the model 1022.

Now that various embodiments of the present invention have been described at a high level, certain embodiments of the present invention will be described in more detail.

As described above, an "acquisition" is the use of a scanner to image a patient, thereby generating one or multiple images (also referred to as acquisition data). The term "acquisition data set" is used herein to refer to the following, which are associated with a particular acquisition: (1) a set of K technical parameters (and their values) that may be used to perform the acquisition; (2) (optionally) a set of descriptors computed from the data obtained by performing the acquisition (e.g., organ labelling or any machine-learning based descriptors computed from the data) and (3) (optionally) one or more non-technical parameters, and their associated values, associated with the acquisition. Each of a plurality of acquisitions may be associated with its own corresponding acquisition descriptor set.

Figure 1:
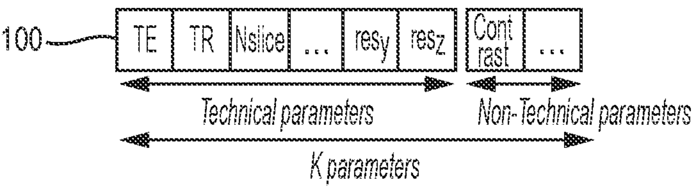
FIG. 1 is a diagram of an example of an acquisition data set according to one embodiment of the present invention.

Referring to FIG. 1, a diagram is shown of an example of an acquisition data set 100 according to one embodiment of the present invention. In the particular example of FIG. 1, the acquisition data set 100 for an MRI acquisition may include one or more of the following parameters (which may include technical parameters and, optionally, one or more non-technical parameters), possibly in addition to other parameters:

Echo Time (TE)
Repetition Time (TR)
Inversion Time
Number of Slices ($N_{slice}$)
Resolution in the x, y, and z dimensions ($res_x$, $res_x$, and $res_x$, respectively)
Flip Angle
Phase encoding direction
Number of averages
Number of phase encoding steps
Percent phase field of view
Percent Sampling
Pixel Bandwidth
Sequence Name
Orientation Matrix
Number of Volumes
Diffusion sensitization parameters
Coil
Contrast/No contrast As a particular example, an acquisition data set for a CT acquisition may include one or more of the following parameters (which may be in addition to any of the parameters listed above):

kVp
mA
Rotation time
mAs
Pitch
Effective mAs
Reconstruction Kernel
Scan Field of View
Image thickness
CTDI
DLP The particular parameters shown in FIG. 1 are merely examples and do not constitute a limitation of the present invention. Instead, any particular acquisition data set may include any parameters in any combination, including parameters not shown in FIG. 1. For example, the parameters in an acquisition data set may include parameters (and corresponding values) derived from HL7 and/or DICOM pixel data and metadata. Example of descriptors derived from the pixel data may include the image SNR, the list of organs in the image, the presence of contrast detected in the image, the type of MR weighting (t1-weighted; t2-weighted; proton density weighted) in the image; or any other feature extracted from the pixel data; but these are merely only examples. Furthermore, the number of parameters K in the acquisition data set may have any value (i.e., the acquisition data set may include any number of parameters). Each of the parameters in the acquisition data set may have a corresponding value, which may change over time. Each acquisition data set may represent a point in a K-dimensional space defined by the values of the acquisition data set's K parameters. Any reference herein to generating, storing, or otherwise processing a "parameter," such as a parameter in an acquisition data set or an examination data set, may include generating, storing, or otherwise processing a value of the parameter.

The term "examination" refers herein to a set of N acquisitions performed on a patient during a particular imaging session. The term "examination data set" refers herein to the following, which are associated with a particular examination: (1) a plurality of acquisition data sets that represent the acquisitions performed in a particular examination corresponding to the examination data set; and (2) (optionally) one or more non-technical parameters, and their associated values, associated with the examination. Each of a plurality of examinations may be associated with its own corresponding examination data set.

One example of non-technical parameters that may be contained within an examination data set are constraints (i.e., maximum values for patient safety), such as radiation dose reference level (e.g., CTDI, DLP), specific absorption rate (SAR), and maximum contrast dose. Other examples of non-technical parameters that may be contained within an examination data set are parameters descriptive of the patient, such as the patient's age and the patient's body mass index (BMI), whether the patient is sedated during an acquisition, disease status of the patient, whether the patient is an in-patient or an out-patient, the emergency level of an examination, and whether an acquisition is performed with contrast.

The acquisitions within an examination may, for example, be ordered. The acquisition data sets within an examination data set may be ordered (e.g., in the same order as the acquisitions within the corresponding examination). The order of the acquisitions within an examination may represent the order in which the acquisitions are intended to be performed and/or actually are performed.

Figure 2:
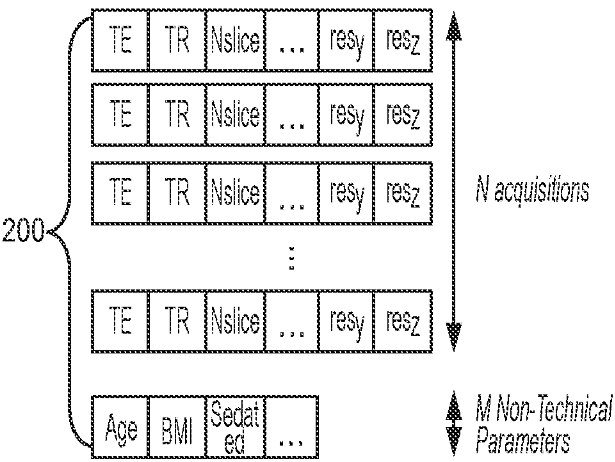
FIG. 2 is a diagram of an example of an examination data set according to one embodiment of the present invention.

Referring to FIG. 2, a diagram is shown of an example of an examination data set 200 according to one embodiment of the present invention. As shown in FIG. 2, the examination data set 200 includes N acquisition data sets, where N may be any number. The examination data set 200 may also include M non-technical parameters associated with the examination. The examination data set 200 may represent a point in (K×N+M)-dimensional space defined by the values of the parameters in the examination data set 200's N acquisition data sets.

Figure 5:
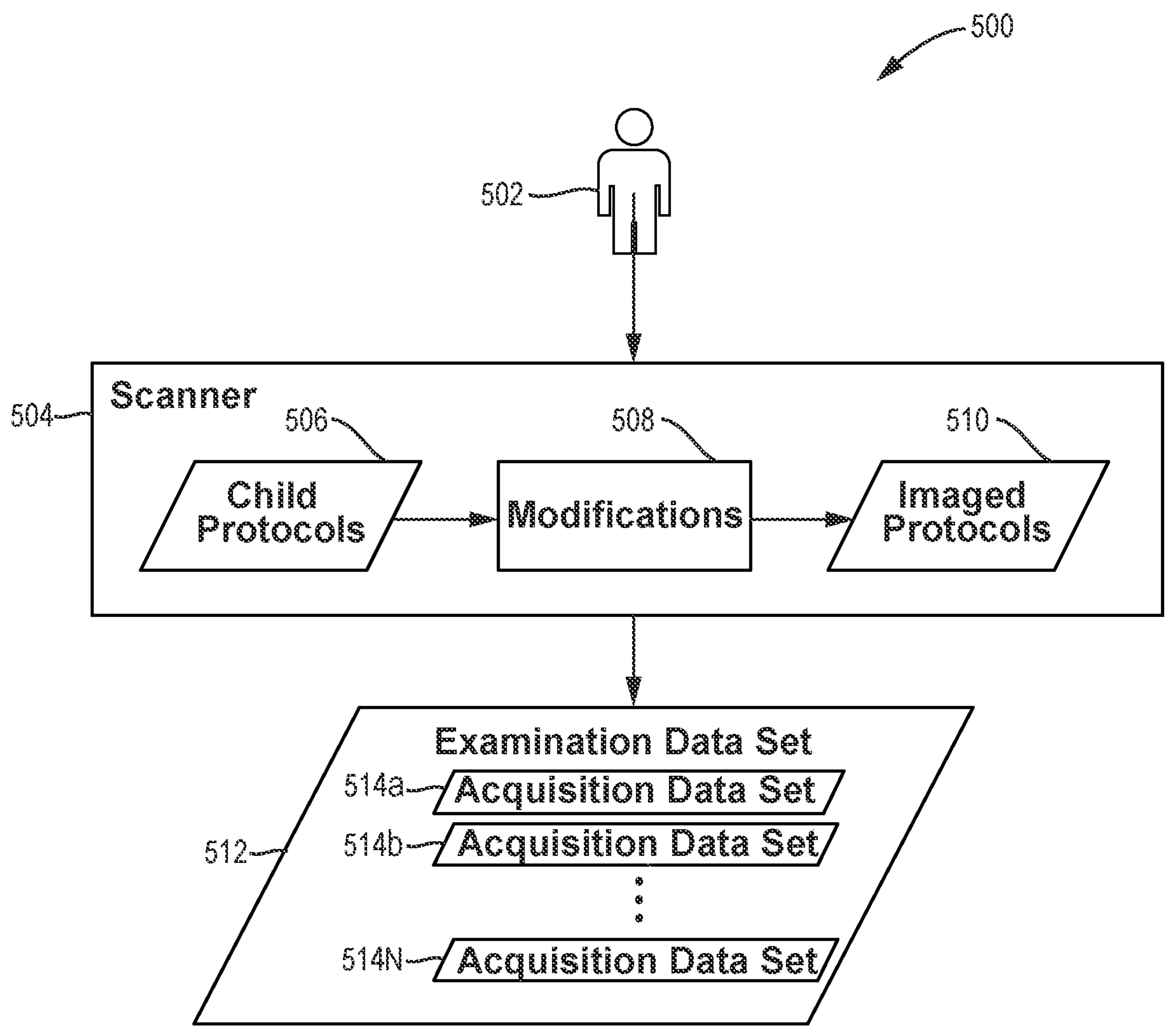
FIG. 5 is a diagram of a system for performing acquisitions according to one embodiment of the present invention.

Referring to FIG. 5, a diagram is shown of a system 500 for performing a plurality of acquisitions in an examination according to one embodiment of the present invention. The system 500 includes a patient 502 and a scanner 504. For purposes of example, the scanner 504 is shown as including a plurality of child protocols 506. In practice, the system 500 may use the child protocols 506 even if they are not stored in the scanner 504. For example, the child protocols 506 may be generated on the fly by the scanner operator. A user (not shown) may make modifications 508 to the child protocols 506 to produce imaged protocols 510 when imaging a patient.

As part of the examination of the patient 502, the scanner 504 performs a plurality of acquisitions of the patient 502. For each acquisition, the scanner 504 images the patient 502 and produces corresponding acquisition data (i.e., images). FIG. 5 shows the resulting examination data set 512, which includes N acquisition data sets 514*a*-N, corresponding to the N acquisitions within the examination.

The term "type of acquisition" refers herein to an acquisition data set having certain parameter values. For example, two different acquisition data sets may have the same parameters, but one or more of those parameters may have different values in the two acquisition data sets. In this case, the two acquisition data sets represent two different types of acquisition. Note that:

- Different clinical conditions may require, or benefit from, different types of acquisitions in order to provide the best insight for each condition.
- The same acquisition technique may be used to perform acquisitions for different clinical conditions, but with different technical parameters, such as for the purpose of assessing different tissue properties.
- It may be desirable or necessary to repeat some acquisitions, such as if the patient moved and the resulting image is blurry.
- It may be desirable or necessary to add a new acquisition, e.g. if there is some suspicion of abnormal tissue and that a new acquisition can help confirm or disconfirm that.

Figure 3:
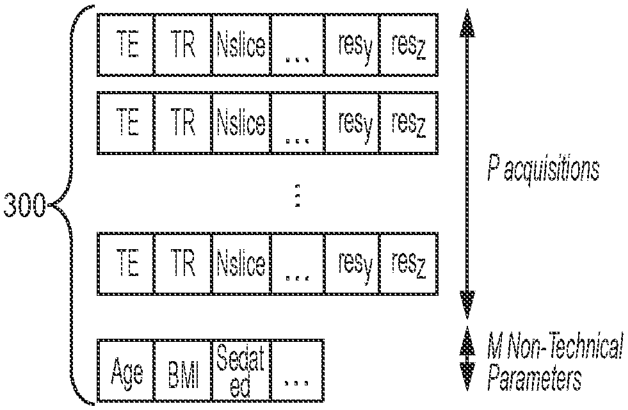
FIG. 3 is a diagram of an example of a parent protocol according to one embodiment of the present invention.

An imaging center or radiology department typically builds ideal protocols (referred to herein as "parent protocols") for each imaging modality (e.g., MRI, CT) and for each organ that describes the imaging need consensus (i.e., list of acquisition data sets). Each parent protocol (and each protocol in general) is defined by its list of acquisition data sets. The imaging need consensus may be different for different patient demographics (e.g., age, BMI). The following are non-limiting examples of parent protocols:

- MR Brain without Contrast—Tumor
- MR Brain without Contrast—Tumor Pediatric
- MR Brain without Contrast—Demyelination
- MR Brain with and without Contrast—Stroke
- MR Knee
- MR Shoulder
- CT Brain
- CT Brain—Fast
- CT Knee Referring to FIG. 3, a diagram is shown of an example of a parent protocol 300 according to one embodiment of the present invention. As shown in FIG. 3, the parent protocol 300 includes N acquisition data sets, where N may be any number. The acquisition data sets within a parent protocol may, for example, be ordered. The order of the acquisitions within a parent protocol may represent the order in which the acquisitions are intended to be performed and/or actually are/were performed according to the parent protocol. When an imaged protocol that is derived from a parent protocol is applied, its acquisitions may be performed in a different order than the order specified in the parent protocol.

As mentioned above, it may not be possible, practical, or desirable to implement a parent protocol without modifications on a particular scanner for a variety of reasons. For example, a scanner may have technical capabilities and/or limitations which impairs its ability to perform acquisitions according to a particular parent protocol. As a result, it may be necessary or desirable to modify the parent protocol and then to perform scans using the modified parent protocol. Such a modified parent protocol is referred to herein as a "child protocol."

A parent protocol may be modified to produce a child protocol in any of a variety of ways, such as one or more of the following:

- Changing the value of a parameter in the parent protocol from a first value to a second value, to produce a child protocol in which that parameter has the second value.
- Removing a parameter from the parent protocol to produce a child protocol which does not include that parameter.
- Adding a parameter to the parent protocol to produce a child protocol which contains the added parameter, even though the parent protocol does not include that parameter.
- Changing the order of two or more acquisitions in the parent protocol to produce a child protocol in which the acquisitions are in a different order than in the parent protocol.

Child protocols often are stored in scanners (like templates) to reduce preparation time and to increase imaging reproducibility and uniformity. A stored child protocol on a scanner may include, for example, each of the child protocol's acquisition data sets, where each of the acquisition data sets includes one or more parameters, and where each of the parameters may or may not include a value. The acquisition data sets in the child protocol stored on the scanner may or may not be ordered.

A unique name may be stored in association with each child protocol in the scanner to facilitate displaying and selecting child protocols. Scanners typically provide a user interface which is capable of displaying names of child protocols that are stored in the scanner, and which enable scanner operators to select, add, delete, and modify child protocols. Before imaging a patient, the scanner operator may use such a scanner user interface to select a particular child protocol that is stored in the scanner.

It may be desirable or necessary, however, for the scanner operator to make one or more modifications to the child protocol to produce a modified protocol (which is an example of an "imaged protocol," as that term is used herein, and result in an examination data set). Such modifications may, for example, include any of the modifications described above in connection with modifying a parent protocol to produce a child protocol. Examples of reasons for modifying a child protocol to produce an imaged protocol include accommodating anatomical features of the patient, needing to repeat one or more acquisitions in the child protocol, and changing the order of acquisitions in the child protocol to prioritize some images over others for the benefit of the reading radiologist.

Figure 4:
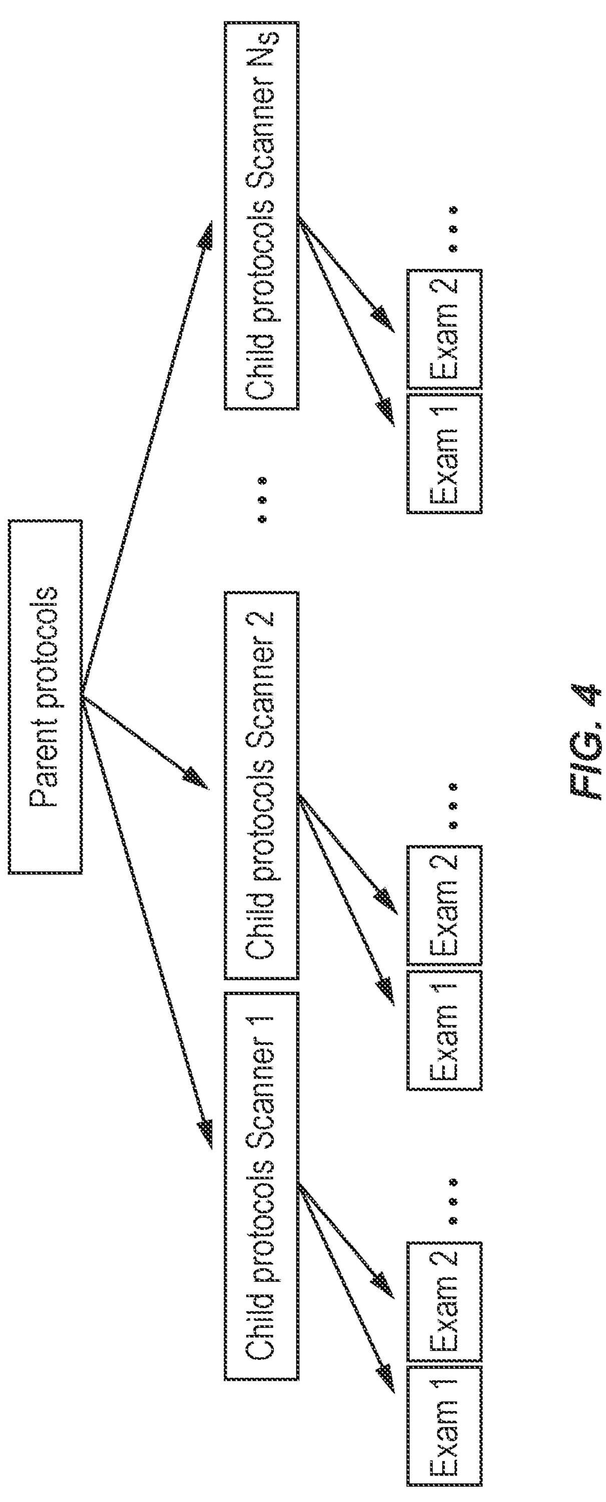
FIG. 4 illustrates relationships among a parent protocol, its child protocols, and its imaged protocols according to one embodiment of the present invention.

FIG. 4 illustrates relationships among a parent protocol, its child protocols, and its imaged protocols (shown in FIG. 4 as examinations) according to one embodiment of the present invention. As shown in FIG. 4, a single parent protocol may have a plurality of child protocols. Each of those child protocols may have one or more of its own imaged protocols. Each of the child protocols may correspond to a distinct scanner. As this implies, all of a child protocol's imaged protocols may be associated with, and stored on, the scanner that is associated with the child protocol.

Note that, in existing systems, the relationships among each parent protocol and its child protocols and imaged protocols (represented by lines connecting the parent protocol to its child protocols, and lines connecting the child protocols to their imaged protocols in FIG. 4) are not stored in any of the scanners or elsewhere. As will be described in more detail below, one of the benefits of embodiments of the present invention is that they may be used to automatically identify, store, and update such relationships over time.

More generally, embodiments of the present invention may be used to automatically generate a model (e.g., the model 1022) that represents relationships among a parent protocol and its child protocols and imaged protocols (such as the relationships illustrated in FIG. 4) by analyzing one or more examination data sets (e.g., the input examination data sets 1012*a*-N and/or the new input examination data sets 1026) representing examinations that have actually been performed using the imaged protocols. Embodiments of the present invention may repeatedly perform such analysis based on new examination data sets as they become available, and automatically update the model (and the relationships that it represents) repeatedly over time.

One of the benefits of embodiments of the present invention is that they may make information about parent protocols explicit, by effectively working backwards from imaged protocols to a representation of a parent protocol, even if there was no explicit representation of that parent protocol previously. Embodiments of the present invention may produce human-readable output representing the resulting parent protocol, thereby aiding in understanding of the parent protocol and of the child protocols and imaged protocols that are descendants of the parent protocol.

Embodiments of the present invention may generate such a model, for example, in the manner disclosed above in connection with FIGS. 10 and 11. In some embodiments, generating the model may, for example, including any of the following. Any reference in the following to performing functions in relation to examinations or acquisitions should be understood to include performing such functions using appropriate data (e.g., examination data sets and/or acquisition data sets).

Embodiments of the present invention may use a metric to compare examinations. Such a metric measures how far apart two examinations are from each other. One challenge in developing such a metric is that two examinations may contain different numbers of acquisitions. If each examination is considered to be a distinct point in a large-dimensional space, the metric must measure a distance between points in spaces of different dimensions. Embodiments of the present invention may compute an embedding of the two examination data sets to transform those examination data sets into a fixed-size representation before computing the distance between the embedded representations. Embodiments of the present inventions may alternatively use a custom distance metric designed to handle examinations with different numbers of acquisitions as described below.

First, consider a distance d(a1, a2) between two acquisitions a1 and a2. Assume that both of the acquisitions a1 and a2 have the same number K of parameters. Embodiments of the present invention may, for example, use any of the following as the distance d (a1, a2):

- the simple L1 or L2 norm;
- a relative distance between each element of a1 and a2 to account for different scale in each element; or
- a more complex metric, e.g., coming from a K-dimensional embedding learned from the data.

Embodiments of the present invention may use the distance d (a1, a2) to compute a distance D(e1, e2) between two examinations e1 and e2 in any of a variety of ways, such as the following. Assume that examination e1 contains $N_1$ examinations and that examination e2 contains $N_2$ acquisitions, where $N_1$ and $N_2$ may or may not be equal to each other.

For each acquisition $a_{1,I}$ of e1 [$a_{1,I}$ in ($a_1 \ldots a_{N1}$)], embodiments of the present invention may evaluate the minimum distance between $a_{1,I}$ and all acquisitions of e2 ($a_{2,1} \ldots a_{2,N2}$). This evaluation may be repeated for each acquisition of e1 and the resulting minimum distances may be aggregated (e.g., summed). In other words:

$$D(e1, e2) = \text{Aggregate}_{for\ each\ a1,I}[\min_{over\ all\ a2,j}(d(a_{1,I}, a_{2,j})]$$

One may also aggregate with the non-technical parameters of e1 and e2. If d^NT(d1, d2) is the distance between non technical parameters, then:

$$D(e1, e2) = \text{Aggregate}\left[d\hat{\ }NT(d1, d2), \text{Aggregate}_{for\ each\ a1,i}[\min_{over\ all\ a2,j}(d(a_{1,i}, a_{2,j})]\right]$$

To make the metric symmetric and to ensure that D(e1, e2)=D(e2, e1), the following metric may be used:

$$D'(e1, e2) = (D(e1, e2) + D(e2, e1))/2$$

Testing of embodiments of the present invention indicates that discrepancies in acquisition descriptors do not have the same weight as each other in the metric. For example, discrepancies in TR (repetition time) often do not have much significance, while discrepancies in contrast often do have much significance. For example, it is important not to associate an image without contrast with an image with contrast. As a result, it may be helpful to assign a relatively high weight to the contrast parameter and a relatively low weight to the TR parameter in the distance metric. Embodiments of the present invention may assign such weights automatically, such as in the following manner.

Embodiments of the present invention may use a weighted sum to tune the importance (weight) of different features (parameters), such as the following:

$$d(a1, a2) = sqrt(\text{sum\_i(w\_i}\|a1i - a2i\|\text{\^{}2)/sum\_i(w\_i)})$$

One approach that may be used by embodiments of the present invention is to estimate the weights using an implicit clustering metric that measures the clustering performance without having to know the true labels. The goal is to learn the weights in order to tune the examination metric (i.e., to focus on the parameters that are important) and optimize some implicit clustering metric describing the clustering performance (e.g., the weights that describe the separability of clusters, the silhouette coefficient, the Calinski-Harabasz coefficient, etc.). The goal, in other words, is to find the weights w that maximize:

ImplicitMetric_{D_w(e1, e2)}

One way to do this is to use an optimization algorithm that does not require explicit formulation of the derivative, such as the Bound Optimization By Quadratic Approximation (BOBYQA) algorithm in the NLopt library, namely to use BOBYQA with:

f(w):

Return (Calculate Implicit Metric with D_w(e1, e2) and ground truth labels)

One approach that may be used by embodiments of the present invention is to estimate the weights using a manually labelled dataset and an explicit clustering metric. Assuming that the true labels are known, the goal is to learn the weight (i.e., tune the examination metric) that lead to a clustering that is as close as possible to the ground truth (e.g., rand index~accuracy or mutual information). One example of this is to use an optimization algorithm that does not require explicit formulation of the derivative, such as BOBYQA, namely to use BOBYQA with:

f(w):

C<-Run clustering algorithm with D_w(e1, e2) Return (Calculate Explicit Metric with C, D_w(e1, e2) and ground truth labels)

Once such an examination distance metric has been developed, it may be used to identify child protocols and/or parent protocols from the set of examinations, such as in any of the following ways. The imaged protocols may be considered to be observations of the unknown child protocols (forward model), and then embodiments of the present invention may be used to invert the forward model and thereby to recover the unknown, underlying child protocols.

Non-supervised learning may be used to learn a set of child protocols based on the set of examination data sets, using the selected examination distance metric. For example, any of a variety of clustering algorithms may use the selected examination distance metric and the set of examinations to identify groups of examinations that are similar to each other in terms of the distance metric between examinations.

Alternatively, for example, supervised learning may be used to learn a set of child protocols based on the set of examinations, using the selected examination distance metric. For example, if each of the examination data sets is labelled with a protocol name, supervised learning may use the selected examination distance metric to train a classifier to automatically recognize the child protocols.

Alternatively, for example, semi-supervised learning may be used to learn a set of child protocols based on the set of examinations, using the selected examination distance metric. For example, non-supervised clustering may be used to generate an initial set of child protocols. Users may then manually correct the resulting labels, and the manually-corrected labels may be used to retrain, and thereby improve, the classifier, thereby resulting in an improved classifier. This process may be repeated any number of times to continue to improve the classifier.

Alternatively, for example, self-supervised learning may be used to learn a set of child protocols based on the set of examinations, using the selected examination distance metric. For example, reinforcement learning may be used to learn the set of child protocols based on the set of examinations, using the selected examination distance metric.

Regardless of which method is used, the result is a set of child protocols that corresponds to the examinations that were used to learn the child protocols.

It may be desirable to update the model (e.g., classifier) developed above over time. For example, parent, child, and imaged protocols may evolve over time. As a result, if the model does not adapt over time to reflect such evolution, the model will become increasingly inaccurate over time. Although a new imaged protocol introduced after generation of the model may at first be seen as a deviation from the model, semi-supervised or self-supervised learning may be used to learn a new child protocol from the new imaged protocol.

The description above explains how embodiments of the present invention may be used to learn child protocols based on imaged protocols. Embodiments of the present invention may also be used to learn parent protocols based on child protocols and/or imaged protocols. In some embodiments of the present invention, child protocols are first learned based on imaged protocols in any of the ways disclosed above, and then one or more parent protocols are learned based on the resulting child protocols (and possibly also based on the imaged protocols). This is an example of what is disclosed elsewhere herein as learning a first set of protocol tags and then learning a second set of protocol tags based on the first set of protocol tags.

Embodiments of the present invention may cluster a plurality of parent protocols, using any of the techniques disclosed above in connection with the child protocols. For example, the child protocols (once they have been learned in any of the ways disclosed above) may be treated as observations of the unknown parent protocols, and then embodiments of the present invention may use clustering between the representative instance of each child protocol to group together the child protocols that are close to each other. Each resulting cluster corresponds to a distinct parent protocol, such that all of the child protocols within a particular cluster are children of the same parent protocol, and such that any two child protocols which are in different clusters are children of different parent protocols.

Embodiments of the present invention may identify or generate a name for a protocol (such as a parent protocol, a child protocol, or an imaged protocol) as follows:

The organ of interest (e.g., MR-Brain/MR-Neck/MR-Abdomen) may be identified by labelling organs by using deep learning and/or other techniques on some or all of the images in the examinations.

Whether there was contrast may be determined by using deep learning and/or other techniques on some or all of the images in the examinations and/or from meta-data (e.g., meta-data from DICOM and/or a scheduling system).

A database of known, labelled protocols (which may be obtained from a plurality of institutions) may be used to identify the most likely protocol name.

Embodiments of the present invention may assess the cloud of examinations for each child protocol (i.e., in each cluster) in order to estimate a non-parametric statistical distribution of the examinations that are associated with each child protocol. This enables embodiments of the present invention to detect deviations from the normal variability in a protocol. Embodiments of the present invention may generate a distribution of normal variability within protocols. Embodiments of the present invention may use that distribution to identify acquisitions and examinations which are outside the range of normal variability.

Embodiments of the present invention may also identify similar child protocols and their associated parent protocol, which allows the same protocol across scanners to be identified and compared. In other words, embodiments of the present invention may identify a plurality of different child protocols on a plurality of scanners, and determine that all of those child protocols are children of the same parent protocol. Once this has been done, embodiments of the present invention may identify differences among different child protocols of the same parent protocol, and harmonize child protocols of the same parent protocol across scanners.

Different protocols have different intrinsic challenges and complexity. For example, when looking at imaging efficacy (ratio of active scan time), it is normal to expect lower efficacy of exams with contrast because the patient has to get out of the scanner and back into the scanner. Some protocols are also intrinsically more challenging to carry out. In order to compare "apples to apples," embodiments of the present invention may measure statistics for each child/parent protocol pair separately, and then compare an instance of that child/parent protocol (i.e., an imaged protocol that is a descendant of the child/parent protocol) to its respective child/parent protocol.

Once the child and parent protocols have been learned, embodiments of the present invention may calculate a heat map for each examination, representing deviations of parameters (i.e., out-of-distribution parameters) from a child protocol and/or a parent protocol. Such heat maps may be generated at the examination level and/or the acquisition level. Such heat maps may be generated for primary (direct) parameters (e.g., DICOM meta-data, RIS) and/or for derived (calculated) parameters (e.g., duration, repeats). In such a heat map, each parameter may be represented by a graphical representation (e.g., circle), in which the area of the graphical representation is a function of (e.g., equal to or proportional to) the percentile of that parameter's value in the statistical distribution previously calculated for the corresponding child protocol or parent protocol. Embodiments of the present invention may generate and provide visual output to the user representing the heatmap for easy understanding and analysis.

More generally, such a heat map may take any form which represents the factors (e.g., parameters in an acquisition or number of acquisitions in an examination) which contributed to the protocol being classified as a deviation, and which assigns, to each such factor, a value that is a function of the degree to which that factor contributed to the protocol being classified as a deviation. A graphical heatmap in which each factor is represented as a shape (e.g., circle) having an area that is a function of the degree to which that factor contributed to the protocol being classified as a deviation is merely one example of this. Another example is a rank list, in which a plurality of factors are listed in increasing or decreasing order of the degree to which each factor contributed to the protocol being classified as a deviation.

Consider the distribution of the degrees to which the factors contributed to the protocol being classified as a deviation. Regardless of the form that the heat map takes, the order of the factors in the heat map may be a function of the order of the factors in the distribution. For example, the sizes of the shapes representing the factors in a graphical heap map may be ordered (e.g., in decreasing or increasing size) as a function of the order of the factors in the distribution. As another example, the order of the factors in a rank list may be a function of (e.g., the same as, or the reverse of) the order of the factors in the distribution.

Other embodiments of the present invention include techniques for transforming the varying-size vectors representing each examination data set into a fixed-size representation by computing an embedding. The embeddings may be used to perform various functions, such as calculating distances between examinations, separating examinations, labeling examinations, predicting values from examinations, and generating new examinations.

One way to create an embedding is to use graph learning. In general, a graph G is composed of a set of nodes (V) and a set of edges (E) between said nodes, where G=(V, E). As is well-known to those having ordinary skill in the art, graphs may be represented in a variety of ways. For example, the edges in a graph may be directed or undirected.

Graphs are especially beneficial/unique in their ability to represent unstructured complex data or systems, and allow us to describe relationships between entities, e.g., in social networks (nodes=one person, edge=whether these persons are "friends"), chemical compounds, drug interactions, knowledge concepts, and interconnected devices, as just some examples.

Graphs may be arbitrary in size and topology. However, one challenge is that they have no fixed node ordering. This can make it difficult to apply traditional machine learning concepts to graphs.

Each of the nodes and edges in a graph may have one or more corresponding features associated with it. This can be useful for encoding information and/or representing relationships. As will be described in more detail below, in embodiments of the present invention, features of nodes/edges may be used by graph learning techniques to internalize important characteristics of the features.

As described above, different examinations (and different protocols) may include different numbers of acquisitions. As a result, different examination data sets and protocols may be of varying size, and therefore be "unstructured" data for which graph learning techniques are better suited than traditional machine learning techniques for most learning tasks.

Figure 8:
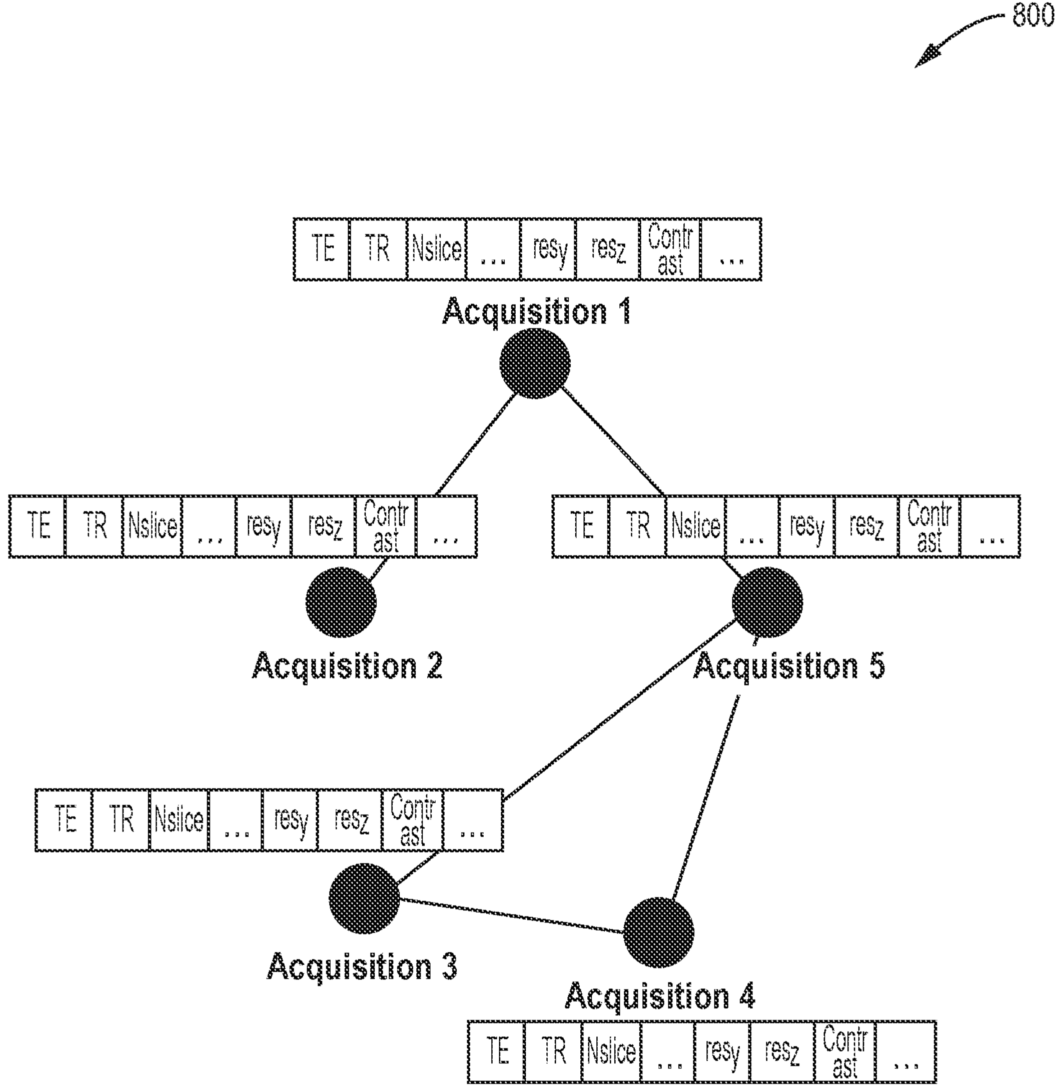
FIG. 8 is a diagram illustration an example of a graph representing an examination data set (or protocol) containing five acquisition data sets according to one embodiment of the present invention.

Embodiments of the present invention include techniques for representing examinations and protocols as graphs and for learning from such graph data. More specifically, embodiments of the present invention may represent an examination or a protocol as a graph, in which each acquisition is a node of the graph. Nodes may have "node features," which may be used to attach information about the corresponding acquisition to each node. For example, the feature vector representing an acquisition (see FIG. 1) is an example of such node features, and may be attached to the node corresponding to the acquisition. In the example shown in FIG. 8, a graph 800 representing an examination or a protocol with five acquisitions includes five nodes representing those acquisitions, in which the feature vector of each acquisition has been attached to its corresponding node.

Embodiments of the present invention may encode relationships between acquisitions in edges in the graph. For example, an edge between two nodes representing two corresponding acquisitions may encode a relationship between those two acquisitions. An example of such a relationship is the distance (or similarity) between the two acquisitions (see the description above of various ways of calculating such a distance). A plurality of edges may encode a plurality of such relationships (e.g., distances) between acquisitions corresponding to the nodes connected by the edges. In the example graph 800 of FIG. 8, edges connect the following node pairs: (1) the nodes representing acquisition numbers 1 and 2; (2) the nodes representing acquisition numbers 1 and 5; (3) the nodes representing acquisition numbers 3 and 4; (4) the nodes representing acquisition numbers 3 and 5; and (5) the nodes representing acquisition numbers 4 and 5. These particular edges are shown merely as examples to aid in understanding.

Embodiments of the present invention may perform the functions disclosed herein on a graph containing such nodes and edges, or the graph may first be binarized before performing such functions. Such binarization may, for example, be performed by applying a threshold value to all of the edges, and then masking (e.g., setting the attached information to zero) any edges whose attached information (e.g., distance) does not satisfy (e.g., exceed) the threshold value. The purpose of such masking of an edge is to ensure that there is no information sharing between these nodes during graph convolution operations involved in graph convolutional networks learning, which is a modeling choice.

Embodiments of the present invention may also attach one or more "edge features" to any edge to encode information about the relationship(s) represented by the edge. For example, an edge feature may encode a label associated with the relationship represented by the edge. As a specific example, an edge feature may be used to identify that the two acquisitions connected by the edge are repeats of an acquisition due to motion, repeats of an acquisition due to another artifact, or are the same type of acquisition (e.g., a fast and slow version of the same acquisition).

Embodiments of the present invention may also attach one or more "graph features" to a graph as a whole. Example of such graph features include information about the examination represented by the graph, such as the M non-technical parameters described above (e.g., patient age, body-mass index, sedated/non-sedated, etc.). Natural language processing (NLP) inputs and/or embeddings calculated from text with NLP techniques may also be used as graph features; this includes text descriptions of protocols, text descriptions of each acquisition, or vector embeddings representing word/sentence embeddings.

Figure 6:
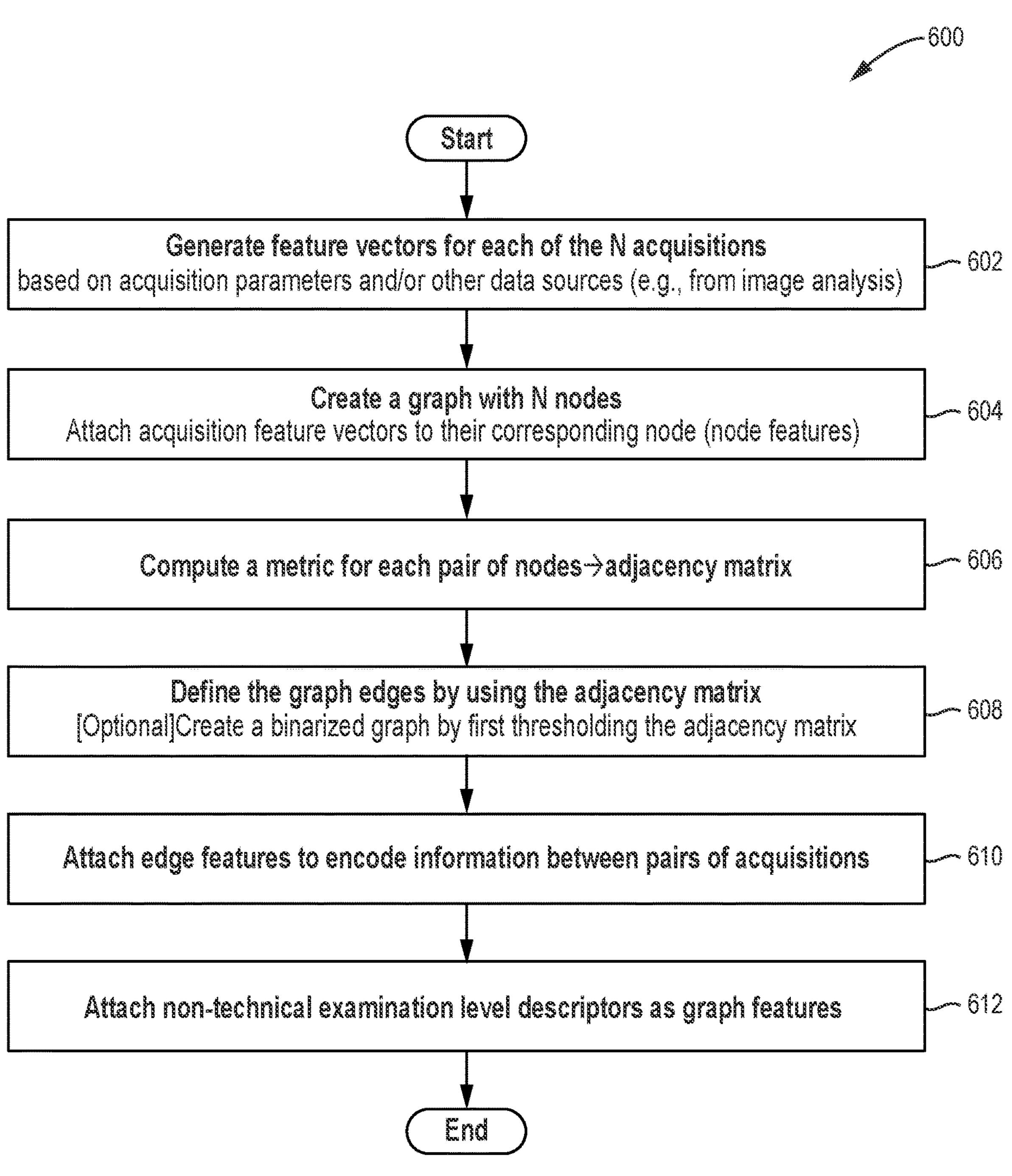
FIG. 6 is a flowchart of a method for converting examination data sets (i.e., a collection of acquisition data sets) into graph data according to one embodiment of the present invention.

Referring to FIG. 6, a flowchart is shown of a method 600 performed by one embodiment of the present invention to generate a graph of the type described above based on a set of acquisitions in an examination or protocol. The method 600 generates feature vectors for each of the N acquisitions in the examination or protocol using any of the techniques disclosed herein, based on the acquisition parameters and/or other data sources (FIG. 6, operation 602). The method 600 attaches each resulting acquisition feature vector to the corresponding node in the graph (FIG. 6, operation 604).

For each pair of nodes' feature vectors, the method 600 computes a metric (e.g., a distance or similarity) based on the pair of feature vectors, such as the cosine similarity, L1 norm, or L2 norm, and generates a graph adjacency matrix, in which each cell at location i, j contains the metric for the pair of nodes i, j (FIG. 6, operation 606). The graph adjacency matrix is an example of a representation of a graph.

The method 600 defines the graph's edges by using the adjacency matrix (FIG. 6, operation 608), and optionally creates a binarized graph by first thresholding the adjacency matrix. The method 600 attaches edge features to edges to encode information between pairs of acquisitions (FIG. 6, operation 610). The method 600 attaches any of the non-technical examination-level descriptors disclosed herein to the graph as "graph features" (FIG. 6, operation 612).

As mentioned above, it can be challenging to apply traditional machine learning to unstructured data. Embodiments of the present invention therefore represent examinations and protocols as graphs, and use graph learning to analyze this type of data. "Graph learning" refers to the application of machine learning to graphs. Graph learning may be applied to perform a variety of functions, such as classifying nodes, predicting relationships between nodes (i.e., the presence of an edge between nodes), and embedding the graph into a different representation that reveals relevant characteristics about the graph, which may then be used to perform functions such as classifying graphs and making predictions. As will be described in more detail below, graph learning involves mapping graphs to manifolds and generating graphs embeddings so that similar graphs are embedded near each other.

When using conventional techniques to extract valuable information from graph data, a common technique is to first manually engineer features. Another technique is to learn those features automatically from the data. Graph learning can automatically generate representative vectors, referred to hereinafter as an "embedding," that contain meaningful information. Embodiments, for example, generate embeddings corresponding to individual nodes in the graph and/or embeddings corresponding to the graph as a whole (or to any sub-graph thereof). As this implies, the embedding representing a particular unit (e.g., node, sub-graph, or graph) may include information derived from that particular unit, and may not include all the information contained in that particular unit, and may include information contained in neighboring units of that particular unit. One benefit of mapping data into an embedding space is that similarities among the data will transcend into the newly-learned manifold. As a result, graphs, sub-graphs, and nodes that have similar characteristics will have embeddings that are close to each other in space.

Embodiments of the present invention may generate embeddings in any of a variety of ways. For example, embodiments of the present invention may generate an embedding using unsupervised learning or supervised learning. The choice of learning method may, for example, be selected based on the specific downstream task that is to be performed using the embedding. For example, if the downstream task is dependent on making a specific classification, then a supervised learning method may be used to generate the embedding. Alternatively, for example, if the downstream application finds patterns and correlations between data points, then an unsupervised learning method may be used to generate the embedding.

Regardless of the type of learning method that is used to generate an embedding, an encoder-like network may be used, which allows for the aggregation of information from connected nodes into a single vector in order to generate the embedding. An embedding vector may be obtained for each node within the graph, and that vector may be converted into a graph embedding using any of a variety of pooling strategies.

When using an unsupervised learning method to generate an embedding, a graph neural network may use a decoder-type network that attempts to reconstruct the graph's adjacency matrix from the encoder output, i.e., the embedding. In such a case, the embedding may be optimized by minimizing the loss between the original and the reconstructed graph. A loss function may be used which quantifies the node similarity between the original and reconstructed space in order to ensure that the embedding vector retains information unique to each respective node.

When using a supervised learning method to generate an embedding, the decoder network may be replaced with a neural network that transforms the embedding vector into a target vector that is representative of specific outputs, e.g., meaningful labels/classes. The embedding may be optimized by minimizing the loss between the predicted output and the target output.

Both unsupervised and supervised learning methods may be used in combination. When a hybrid learning method is used to generate an embedding, the generated embedding may be fed through a decoder network and a neural network, or a set of neural networks, in parallel. The embedding may be optimized by combining the loss between the predicted output and target output (from the supervised method) and the loss between the original and reconstructed space (from the unsupervised method).

Embodiments of the present invention may use the generated embeddings in combination with embeddings obtained from natural language processing methods for further downstream processing tasks. Referring to FIG. 6, if examination-level protocol text is available, embodiments of the present invention may use sequence-to-sequence or transformer models to generate new text-level embeddings. These embeddings may be used in combination with graph embeddings for downstream tasks.

Once embodiments of the present invention have generated one or more embeddings, those embeddings representing examinations or protocols may be used by one or more downstream applications to perform a variety of functions, such as:

- Using embeddings for separation tasks. Such tasks relate to using machine learning algorithms for the purpose of separating the embeddings in order to distinguish/identify distinct protocols and sub-protocols (e.g., "learn the protocols of an institution from its data"). Such separation may, for example, be performed at the examination/protocol level or at the scanner level.
- Using embeddings for classification/labeling tasks. Such tasks relate to assigning (or predicting) specific descriptors to embeddings (e.g., predicting a class from an embedding such as predicting the body part, the CPT code for insurance purpose, the protocol name (e.g., mapping to different lexicons, e.g., Radlex), the acquisitions involved, the MRI scanner used, the department requesting the protocol, determining whether the protocol fulfills the "appropriateness criteria" from the American College of Radiology, or recommending a certain scanner for a given protocol and an indication, merely as examples).
- Using embeddings for regression tasks. Such tasks relate to predicting a specific value from embeddings, such as the protocol duration, the room utilization efficiency, the slot utilization efficiency, the protocol efficiency, the patient preparation time needed, the radiologist turn-around time, the time it takes for radiologists to read the exam, the time from order to exam, or the patient age, merely as examples.
- Using embeddings for generative/recommender tasks. Such tasks correspond to reversing the embedding process, or combining multiple tasks for the purpose of generating recommendations and or generating new protocols or examinations, such as generating an equivalent protocol for a different scanner, generating an alternative protocol for outlier cases (e.g., neonate, obese patient, patient with implants), standardizing protocols across all scanners, generating a fast/slow version of a protocol, combining protocols, or generating a name for the protocol, merely as examples.

Some examples of separation tasks are the following:

- Protocol Identification for a scanner. In an unsupervised fashion, embodiments of the present invention may use clustering algorithms on embeddings to automatically learn groups of examinations/protocols with similar properties (occupying the same embedding space), also referred to herein as scanner imaging protocols (or child protocols).
- Protocol identification across scanners. Embodiments of the present invention may compare embeddings across scanners to learn parent protocols.
- Out of Distribution and New Protocols. Using the specific clusters (which correlate with the parent and child protocols discussed previously) that arise from the distribution of exam embeddings, various algorithms may be used to determine how confident we are that a new given examination belongs to a cluster. This may be used, for example, to determine potentially wrongfully labeled exams and/or identify protocol deviations (e.g., that the technologist changed some parameters). This may also be used, for example, to identify that new protocols have been created. For example, if there is an increase in the determination of "out of distribution" instances within a cluster, this may be the result of a new protocol having been created, which needs to be identified.
- Protocol harmonization across scanners. Having both the parent protocol and child protocol allows evaluation of differences across scanners for a same protocol, which is useful for protocol harmonization.

Some examples of classification/labelling tasks are the following:

- Exam/protocol name. This involves associating a name with an examination/protocol, based on its characteristics.
- Assign/predict a CPT code to an examination/protocol. This involves assigning a CPT code to an examination/protocol, based on its characteristics.
- Add descriptor. This involves identifying and adding a specific descriptor that makes a cluster unique, such as an anatomical descriptor or a contrast descriptor.

Regression tasks may combine the embedding representing a protocol/examination with a regression model to build models that predict continuous values, such as any one or more of the following: protocol/examination duration, protocol/examination preparation time, protocol examination reading time by radiologists, image quality, and diagnostic value.

Generative/recommendation tasks may be used to reverse the process of encoding graph information into an embedding, to generate (an approximation of) the information that was initially encoded into the embedding. For example, at the node level, generative/recommendation tasks may generate the specific acquisition parameters that were encoded. Such information may then be propagated to the graph level and then used to generate an entire protocol for each examination. Some examples of generative/recommendation tasks are the following:

- Generate nominal protocol-acquisition and their parameters. This involves generating, from an embedding, the graph that corresponds to it.
- Generate a harmonized version of the same protocol on a different scanner.

Smart Recommendations. By combining various outputs from previously-described tasks, a learning pipeline may be dedicated to making specific recommendations. Given that the embeddings have been trained to aggregate valuable information at the examination/protocol level, they are a good starting dimension reduction to run simulations on and to determine the optimal recommendation for a given task.

Figure 9:
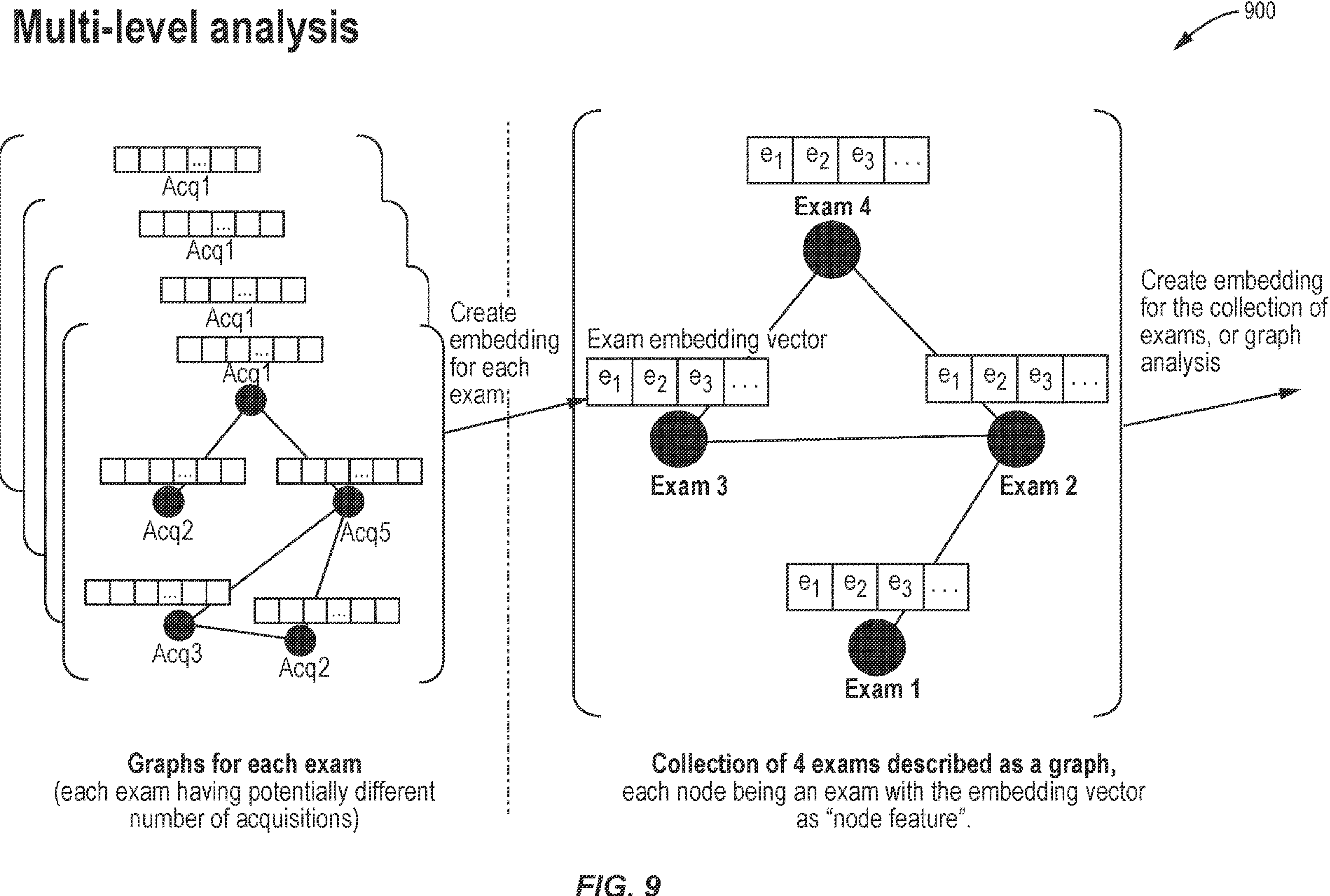
FIG. 9 is a diagram illustrating multi-level analysis of examination data sets (or protocols) described by their graphs and subsequently by their embeddings according to one embodiment of the present invention.

As shown, for example, in FIG. 9, embodiments of the present invention include techniques for representing collections of examinations or collections of protocols as graphs and for learning from such graph data, such as for solving the parent protocol learning problem from child protocols, or learning across different hospitals.

Figure 7:
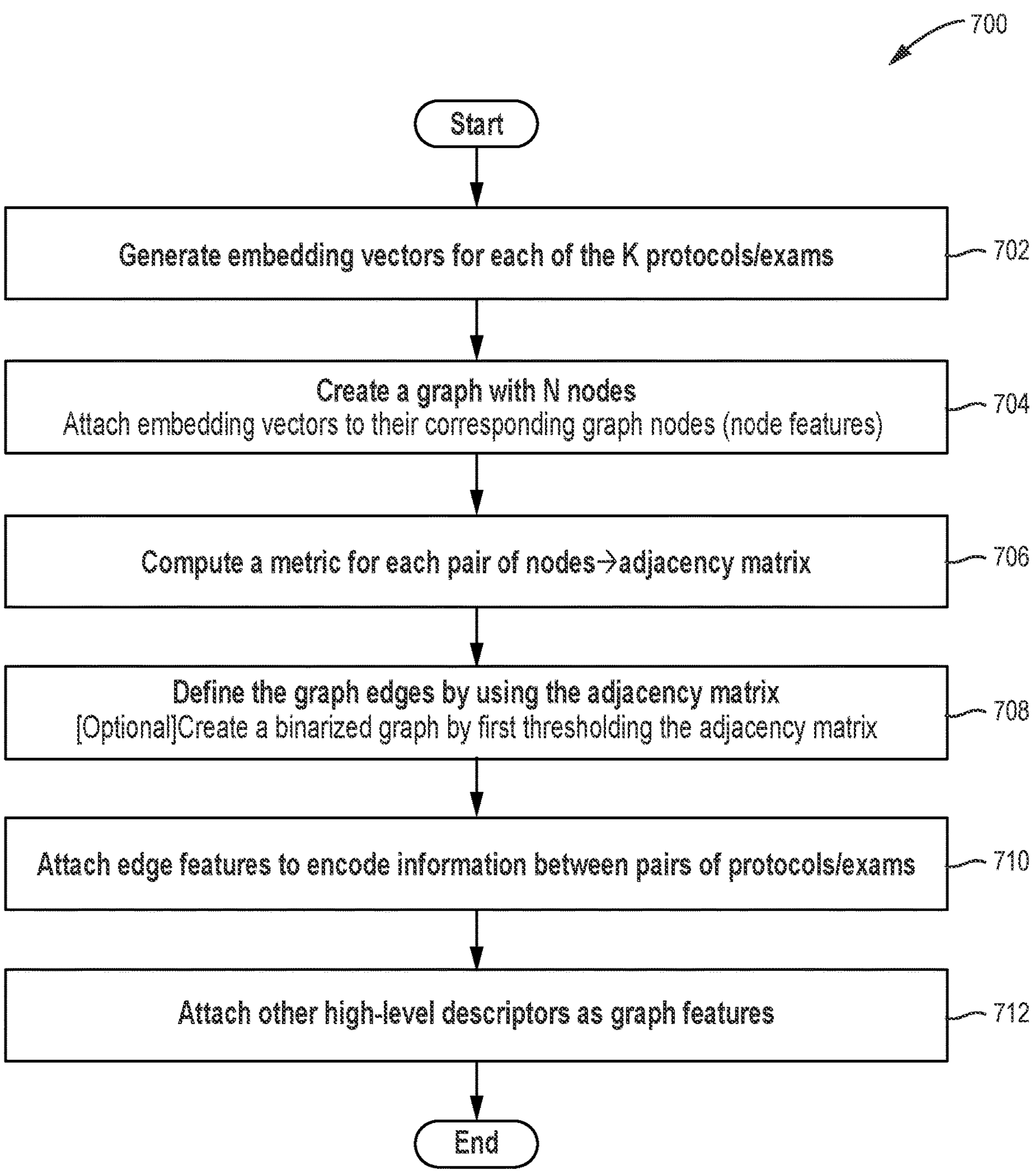
FIG. 7 is a flowchart of a method for converting a collection of examination data sets or protocols into embeddings, and then embeddings into graph data according to one embodiment of the present invention.

For example, FIG. 7 is a flowchart of a method 700 for converting a collection of examinations or protocols into graph data according to one embodiment of the present invention. More specifically, embodiments of the present invention may represent each protocol (or examination) in a collection as a corresponding node in a graph. More specifically, the method 700 may first generate embedding vectors for each of K protocols or examinations using any of the techniques disclosed herein (FIG. 7, operation 702). The method 700 may also create a graph with N nodes, and attach each of the embedding vectors to a corresponding node in the graph (FIG. 7, operation 704). In this embodiment, the embedding vectors are examples of "node features," which attach information about the corresponding protocol (e.g., respective examination) to each node.

Embodiments of the present invention may encode relationships between protocols/examinations in edges in the graph. For example, an edge between two nodes representing two corresponding protocols may encode a relationship between those two protocols. An example of such a relationship is the distance (or similarity) between the two protocols (distance between the embedding vectors set as nodes).

For example, the method 700 may, for each pair of nodes' embedding vectors, compute a metric based on the pair of embedding vectors (FIG. 7, operation 706). The method 700 may generate a graph adjacency matrix, in which each cell at location i, j contains the metric for the pair of nodes i, j. The graph adjacency matrix is an example of a representation of a graph.

The method 700 may define the graph's edges by using the adjacency matrix (FIG. 7, operation 708), and optionally create a binarized graph by first thresholding the adjacency matrix. The method 700 may attach one or more "edge features" to any edge to encode information about the relationship(s) represented by the edge (FIG. 7, operation 710). For example, an edge feature may encode a label associated with the relationship represented by the edge. As a specific example, an edge feature may be used to identify that the two protocols/examinations connected by the edge are from the same body part (e.g., Neuro, Chest, Lower extremity, etc.) or are from the same institution, merely as two examples.

The method 700 may attach one or more other high-level descriptors to the graph as a whole as "graph features" (FIG. 7, operation 712). Examples of such graph features include information about the collection of protocols/examinations represented by the graph, such as the institution or the body part, merely as two examples.

FIG. 9 illustrates an example system 900 in which each of a plurality of graphs represents a corresponding examination. The left side of FIG. 9 shows the plurality of graphs at a low level (examination instances), from which embedding vectors are calculated, and the right side of FIG. 9 shows one of the plurality of graphs to encode the collection of examinations, for purposes of example. The system 900 may use any of the techniques disclosed herein to create, based on the plurality of graphs, an embedding for the plurality of examinations.

In some embodiments, the techniques described herein include a method performed by at least one computer processor executing computer program instructions stored on at least one non-transitory computer-readable medium, the method including: (A) receiving a plurality of input examination data sets created by performing a plurality of imaging examinations of at least one patient on at least one scanner, wherein each of the plurality of input examination data sets includes a plurality of acquisition data sets, wherein each acquisition data set A in the plurality of acquisition data sets includes a corresponding plurality of values of a plurality of technical parameters that were used to perform the acquisition that generated the acquisition data set A; and (B) learning, based on the plurality of input examination data sets, a model of imaging protocols.

The model may capture common features across the plurality of input examination data sets. The model may regroup examination data sets, within the plurality of input examination data sets, with common features under a common protocol tag, wherein learning the model includes generating a plurality of protocol tags.

The method may further include: (C) receiving a plurality of new input examination data sets; and (D) generating, using the model, a plurality of protocol tags, wherein each of the plurality of protocol tags describes a corresponding set of common features within the plurality of new input examination data sets.

The learning may include supervised learning and/or unsupervised learning.

Each tag T in the plurality of protocol tags may describe a corresponding set of examination data sets in the plurality of input examination data sets, wherein the set of examination data sets corresponding to tag T includes a plurality of acquisition data sets that share a corresponding set of common features within the plurality of input examination data sets.

The learning may include: (B)(1) learning a first set of protocol tags from the plurality of input examination data sets; and (B)(2) learning a second set of protocol tags from the plurality of input examination data sets and the first set of protocol tags, wherein the second set of protocol tags describes a corresponding set of common features of a corresponding plurality of protocol tags within the first set of protocol tags.

The learning may includes, for N=1: (B)(1) learning an Nth set of protocol tags from the plurality of input examination data sets and from any previously-learned set(s) of protocol tags for N≥1, wherein the Nth set of protocol tags describes a corresponding set of common features of a corresponding plurality of (N−1)-level protocol tags; (B)(2) determining whether a termination criterion has been satisfied; (B)(3) if the termination criterion has been satisfied, then terminating the learning; (B)(4) if the termination criterion has not been satisfied, then: (B)(4)(a) incrementing N; and (B)(4)(b) returning to (B)(1).

Operation (B) may include learning, based on the plurality of input examination data sets, a classifier or clustering algorithm for identifying characteristics of protocol tags; and wherein learning the model may include using the classifier or clustering algorithm to learn the plurality of protocol tags.

The method may further include: (C) identifying, for each of the plurality of protocol tags, a corresponding organ of interest, thereby identifying a plurality of organs of interest corresponding to the plurality of protocol tags; and (D) identifying, for each of the plurality of protocol tags, a label.

Operation (C) may include identifying the plurality of organs of interest corresponding to the plurality of protocol tags by applying learning to a plurality of images in the plurality of input examination data sets.

Operation (D) may include identifying the label associated with each of the plurality of protocol tags based on a set of labelled examination data sets.

The plurality of protocol tags may include a plurality of embeddings of fixed size.

Operation (A) may include: (A)(1) generating, for each input examination data set in the plurality of input examination data sets, a corresponding graph, including: (A)(1)(a) for each of a plurality of nodes in the graph corresponding to a plurality of acquisition data sets in the input examination data set, storing information about the acquisition corresponding to the node; and (A)(1)(b) for each pair of nodes in the corresponding graph, generating and storing an edge in the graph representing information about a relationship between the pair of nodes; thereby generating a plurality of graphs corresponding to the plurality of input examination data sets.

Operation (B) may include: performing learning based on the corresponding plurality of graphs to generate a corresponding plurality of embeddings representing a plurality of protocol tags.

The method may further include, after performing (A) and (B): (C) receiving a plurality of new input examination data sets created by performing a new plurality of imaging examinations of at least one patient on at least one scanner; and (D) learning, based on the plurality of new input examination data sets, an updated version of the model of imaging protocols.

The method may further include: (C) generating, for the corresponding plurality of embeddings, a graph corresponding to the corresponding plurality of embeddings, including: (C)(1)(a) for each node in a plurality of nodes in the graph corresponding to the plurality of embeddings, storing information about an embedding corresponding to the node; and (C)(1)(b) for each pair of nodes in the corresponding graph, generating and storing an edge in the corresponding graph representing information about a relationship between the pair of embeddings.

Operation (B) may further include: performing learning on the corresponding graph generated in (C) to generate a plurality of high level embeddings.

The method may further include: (C) generating, based on the plurality of embeddings, at least one synthetic examination data set, wherein the plurality of input examination data sets does not include the synthetic examination data set.

In some embodiments, the techniques described herein include a system including at least one non-transitory computer-readable medium having computer program instructions stored thereon, the computer program instructions being executable by at least one computer processor to perform a method, the method including: (A) receiving a plurality of input examination data sets created by performing a plurality of imaging examinations of at least one patient on at least one scanner, wherein each of the plurality of input examination data sets includes a plurality of acquisition data sets, wherein each acquisition data set A in the plurality of acquisition data sets includes a corresponding plurality of values of a plurality of technical parameters that were used to perform the acquisition that generated the acquisition data set A, and (B) learning, based on the plurality of input examination data sets, a model of imaging protocols.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention may apply deep learning to learn child protocols and parent protocols. Such functions are inherently rooted in computer technology and cannot be performed mentally or manually.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAS (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

Any step or act disclosed herein as being performed, or capable of being performed, by a computer or other machine, may be performed automatically by a computer or other machine, whether or not explicitly disclosed as such herein. A step or act that is performed automatically is performed solely by a computer or other machine, without human intervention. A step or act that is performed automatically may, for example, operate solely on inputs received from a computer or other machine, and not from a human. A step or act that is performed automatically may, for example, be initiated by a signal received from a computer or other machine, and not from a human. A step or act that is performed automatically may, for example, provide output to a computer or other machine, and not to a human.

The terms "A or B," "at least one of A or/and B," "at least one of A and B," "at least one of A or B," or "one or more of A or/and B" used in the various embodiments of the present disclosure include any and all combinations of words enumerated with it. For example, "A or B," "at least one of A and B" or "at least one of A or B" may mean: (1) including at least one A, (2) including at least one B, (3) including either A or B, or (4) including both at least one A and at least one B.

What is claimed is:

1. A method performed by at least one computer processor executing computer program instructions stored on at least one non-transitory computer-readable medium, the method comprising:

(A) receiving a plurality of input examination data sets created by performing a plurality of imaging examinations of at least one patient on at least one scanner, wherein each examination E in the plurality of input examination data sets comprises a plurality of acquisition data sets that were acquired in examination E, wherein each acquisition data set A in each examination E comprises a corresponding plurality of values of a plurality of technical parameters that were used to perform the acquisition that generated the acquisition data set A, and (B) learning, based on the plurality of input examination data sets, a model of imaging protocols;

wherein (A) comprises:

(A)(1) generating, for each input examination data set in the plurality of input examination data sets, a corresponding graph, comprising:

(A)(1)(a) for each of a plurality of nodes in the graph corresponding to a plurality of acquisition data sets in the input examination data set, storing information about the acquisition corresponding to the node;

(A)(1)(b) for each pair of nodes in the corresponding graph, generating and storing an edge in the graph representing information about a relationship between the pair of nodes;

thereby generating a plurality of graphs corresponding to the plurality of input examination data sets.

2. The method of claim 1, wherein the model captures common features across the plurality of input examination data sets.

3. The method of claim 2, wherein the model regroups examination data sets, within the plurality of input examination data sets, with common features under a common protocol tag in the plurality of protocol tags.

4. The method of claim 3, wherein each tag T in the plurality of protocol tags describes a corresponding set of examination data sets in the plurality of input examination data sets, wherein the set of examination data sets corresponding to tag T includes a plurality of acquisition data sets that share a corresponding set of common features within the plurality of input examination data sets.

5. The method of claim 3, further comprising:

(C) identifying, for each of the plurality of protocol tags, a corresponding organ of interest, thereby identifying a plurality of organs of interest corresponding to the plurality of protocol tags; and (D) identifying, for each of the plurality of protocol tags, a label.

6. The method of claim 5, wherein (C) comprises identifying the plurality of organs of interest corresponding to the plurality of protocol tags by applying learning to a plurality of images in the plurality of input examination data sets.

7. The method of claim 5, wherein (D) comprises identifying the label associated with each of the plurality of protocol tags based on a set of labelled examination data sets.

8. The method of claim 3, wherein the plurality of protocol tags comprises a plurality of embeddings of fixed size.

9. The method of claim 8, further comprising:

(C) generating, based on the plurality of embeddings, at least one synthetic examination data set, wherein the plurality of input examination data sets does not include the synthetic examination data set.

10. The method of claim 1, further comprising:

(C) receiving a plurality of new input examination data sets; and (D) generating, using the model, a plurality of protocol tags, wherein each of the plurality of protocol tags describes a corresponding set of common features within the plurality of new input examination data sets.

11. The method of claim 1, wherein the learning comprises supervised learning.

12. The method of claim 1, wherein the learning comprises unsupervised learning.

13. The method of claim 1, wherein the learning comprises:

(B)(1) learning a first set of protocol tags from the plurality of values of the plurality of technical parameters in the plurality of input examination data sets; and (B)(2) learning a second set of protocol tags from the plurality of values of the plurality of technical parameters in the plurality of input examination data sets and the first set of protocol tags, wherein the second set of protocol tags describes a corresponding set of common features of a corresponding plurality of protocol tags within the first set of protocol tags.

14. The method of claim 1, wherein the learning comprises, for N=1:

(B)(1) learning an Nth set of protocol tags from the plurality of values of the plurality of technical parameters in the plurality of input examination data sets and from any previously-learned set(s) of protocol tags for N≥1, wherein the Nth set of protocol tags describes a corresponding set of common features of a corresponding plurality of (N−1)-level protocol tags;

(B)(2) determining whether a termination criterion has been satisfied;

(B)(3) if the termination criterion has been satisfied, then terminating the learning;

(B)(4) if the termination criterion has not been satisfied, then:

(B)(4)(a) incrementing N; and (B)(4)(b) returning to (B)(1).

15. The method of claim 1, wherein (B) comprises learning, based on the plurality of values of the plurality of technical parameters in the plurality of input examination data sets, a classifier or clustering algorithm for identifying characteristics of protocol tags; and wherein learning the model comprises using the classifier or clustering algorithm to learn the plurality of protocol tags.

16. The method of claim 1, wherein (B) comprises: performing learning based on the plurality of values of the plurality of technical parameters in the corresponding plurality of graphs to generate a corresponding plurality of embeddings representing a plurality of protocol tags.

17. The method of claim 16, further comprising:

(C) generating, for the corresponding plurality of embeddings, a graph corresponding to the corresponding plurality of embeddings, comprising:

(C)(1)(a) for each node in a plurality of nodes in the graph corresponding to the plurality of embeddings, storing information about an embedding corresponding to the node;

(C)(1)(b) for each pair of nodes in the corresponding graph, generating and storing an edge in the corresponding graph representing information about a relationship between the pair of embeddings.

18. The method of claim 17, further comprising: performing learning on the corresponding graph generated in (C) to generate a plurality of high level embeddings.

19. The method of claim 1, further comprising, after performing (A) and (B):

(C) receiving a plurality of new input examination data sets created by performing a new plurality of imaging examinations of at least one patient on at least one scanner;

(D) learning, based on the plurality of values of the plurality of technical parameters in the plurality of new input examination data sets, an updated version of the model of imaging protocols.

20. A system comprising at least one non-transitory computer-readable medium having computer program instructions stored thereon, the computer program instructions being executable by at least one computer processor to perform a method, the method comprising:

(A) receiving a plurality of input examination data sets created by performing a plurality of imaging examinations of at least one patient on at least one scanner, wherein each examination E in the plurality of input examination data sets comprises a plurality of acquisition data sets that were acquired in examination E, wherein each acquisition data set A in each examination E comprises a corresponding plurality of values of a plurality of technical parameters that were used to perform the acquisition that generated the acquisition data set A, and (B) learning, based on the plurality of input examination data sets, a model of imaging protocols;

wherein (A) comprises:

(A)(1) generating, for each input examination data set in the plurality of input examination data sets, a corresponding graph, comprising:

(A)(1)(a) for each of a plurality of nodes in the graph corresponding to a plurality of acquisition data sets in the input examination data set, storing information about the acquisition corresponding to the node;

(A)(1)(b) for each pair of nodes in the corresponding graph, generating and storing an edge in the graph representing information about a relationship between the pair of nodes;

thereby generating a plurality of graphs corresponding to the plurality of input examination data sets.

21. A method performed by at least one computer processor executing computer program instructions stored on at least one non-transitory computer-readable medium, the method comprising:

(A) receiving a plurality of input examination data sets created by performing a plurality of imaging examinations of at least one patient on at least one scanner, wherein each examination E in the plurality of input examination data sets comprises a plurality of acquisition data sets that were acquired in examination E, wherein each acquisition data set A in each examination E comprises a corresponding plurality of values of a plurality of technical parameters that were used to perform the acquisition that generated the acquisition data set A, and (B) learning, based on the plurality of input examination data sets, a model of imaging protocols;

wherein the learning comprises, for N=1:

(B)(1) learning an Nth set of protocol tags from the plurality of values of the plurality of technical parameters in the plurality of input examination data sets and from any previously-learned set(s) of protocol tags for N≥1, wherein the Nth set of protocol tags describes a corresponding set of common features of a corresponding plurality of (N−1)-level protocol tags;

(B)(2) determining whether a termination criterion has been satisfied;

(B)(3) if the termination criterion has been satisfied, then terminating the learning;

(B)(4) if the termination criterion has not been satisfied, then:

(B)(4)(a) incrementing N; and (B)(4)(b) returning to (B)(1).

22. A system comprising at least one non-transitory computer-readable medium having computer program instructions stored thereon, the computer program instructions being executable by at least one computer processor to perform a method, the method comprising:

(A) receiving a plurality of input examination data sets created by performing a plurality of imaging examinations of at least one patient on at least one scanner, wherein each examination E in the plurality of input examination data sets comprises a plurality of acquisition data sets that were acquired in examination E, wherein each acquisition data set A in each examination E comprises a corresponding plurality of values of a plurality of technical parameters that were used to perform the acquisition that generated the acquisition data set A, and (B) learning, based on the plurality of input examination data sets, a model of imaging protocols;

wherein the learning comprises, for N=1:

(B)(1) learning an Nth set of protocol tags from the plurality of values of the plurality of technical parameters in the plurality of input examination data sets and from any previously-learned set(s) of protocol tags for N≥1, wherein the Nth set of protocol tags describes a corresponding set of common features of a corresponding plurality of (N−1)-level protocol tags;

(B)(2) determining whether a termination criterion has been satisfied;

(B)(3) if the termination criterion has been satisfied, then terminating the learning;

(B)(4) if the termination criterion has not been satisfied, then:

(B)(4)(a) incrementing N; and (B)(4)(b) returning to (B)(1).

* * * * *